(12) United States Patent
Alonso et al.

(10) Patent No.: US 9,698,841 B2
(45) Date of Patent: Jul. 4, 2017

(54) METHOD AND APPARATUS FOR ASSOCIATING RADIO FREQUENCY IDENTIFICATION TAGS WITH PARTICIPANTS

(71) Applicant: ZIH Corp., Lincolnshire, IL (US)

(72) Inventors: Rodrigo Alonso, Gilroy, CA (US); Belinda Turner, Germantown, MD (US); Aitan Ameti, Rockville, MD (US); David Senerchia, North Kingstown, RI (US)

(73) Assignee: ZIH Corp., Lincolnshire, IL (US)

(*) Notice: Subject to any disclaimer, the term of this patent is extended or adjusted under 35 U.S.C. 154(b) by 0 days.

(21) Appl. No.: 14/297,361

(22) Filed: Jun. 5, 2014

(65) Prior Publication Data
US 2015/0002272 A1   Jan. 1, 2015

Related U.S. Application Data

(60) Provisional application No. 61/831,990, filed on Jun. 6, 2013.

(51) Int. Cl.
G06Q 10/08    (2012.01)
H04B 1/10     (2006.01)
(Continued)

(52) U.S. Cl.
CPC ....... *H04B 1/1036* (2013.01); *A63B 24/0021* (2013.01); *A63B 24/0062* (2013.01);
(Continued)

(58) Field of Classification Search
CPC ..... A63F 13/30; A63B 71/06; A63B 71/0619; A63B 71/0622; A63B 24/0062;
(Continued)

(56) References Cited

U.S. PATENT DOCUMENTS 3,732,500 A   5/1973   Dishal et al.
5,119,104 A   6/1992   Heller
(Continued)

FOREIGN PATENT DOCUMENTS

EP   1235077 A2   8/2002
EP   1253438 A2   10/2002
(Continued)

OTHER PUBLICATIONS

International Search Report and Written Opinion from International Application No. PCT/US2014/040940 dated Dec. 17, 2014.
(Continued)

*Primary Examiner* — Steven Lim
*Assistant Examiner* — Mancil Littlejohn, Jr.

(57) ABSTRACT

Systems, methods, apparatuses, and computer readable media are disclosed for associating a radio frequency identification tag with a participant. In one embodiment, a method is provided for associating an unassociated RF location tag with a participant. The method may include determining an unassociated RF location tag to be associated with the participant, receiving sensor derived data from one or more sensors, determining an identity of the particular participant using the sensor derived data, and associating the identity of the particular participant with the unassociated RF location tag.

18 Claims, 11 Drawing Sheets

(51) Int. Cl.

| | | |
|---|---|---|
| *G06F 17/30* | (2006.01) | |
| *H04L 29/08* | (2006.01) | |
| *A63B 24/00* | (2006.01) | |
| *G06K 7/10* | (2006.01) | |
| *G08C 17/02* | (2006.01) | |
| *H04B 1/7097* | (2011.01) | |
| *H04W 4/02* | (2009.01) | |
| *A63B 71/06* | (2006.01) | |
| *G06K 9/00* | (2006.01) | |
| *G06F 19/00* | (2011.01) | |
| *G06N 5/02* | (2006.01) | |
| *H04L 12/26* | (2006.01) | |
| *G06Q 50/20* | (2012.01) | |
| *G09B 19/00* | (2006.01) | |
| *H04B 1/7163* | (2011.01) | |
| *H04B 1/719* | (2011.01) | |
| *G06Q 50/22* | (2012.01) | |
| *H04Q 9/00* | (2006.01) | |
| *G06K 17/00* | (2006.01) | |
| *G06Q 90/00* | (2006.01) | |

(52) U.S. Cl.
CPC .......... *A63B 71/06* (2013.01); *A63B 71/0619* (2013.01); *A63B 71/0622* (2013.01); *G06F 17/3087* (2013.01); *G06F 17/30864* (2013.01); *G06F 17/30876* (2013.01); *G06F 19/3437* (2013.01); *G06K 7/10227* (2013.01); *G06K 7/10297* (2013.01); *G06K 7/10306* (2013.01); *G06K 7/10366* (2013.01); *G06K 9/00342* (2013.01); *G06N 5/02* (2013.01); *G06Q 50/20* (2013.01); *G06Q 50/22* (2013.01); *G08C 17/02* (2013.01); *G09B 19/0038* (2013.01); *H04B 1/7097* (2013.01); *H04B 1/719* (2013.01); *H04B 1/71635* (2013.01); *H04B 1/71637* (2013.01); *H04L 43/04* (2013.01); *H04L 67/12* (2013.01); *H04Q 9/00* (2013.01); *H04W 4/02* (2013.01); *A63B 24/00* (2013.01); *A63B 2024/0025* (2013.01); *A63B 2220/836* (2013.01); *A63B 2225/50* (2013.01); *A63B 2225/54* (2013.01); *G06K 2017/0045* (2013.01); *G06Q 90/00* (2013.01)

(58) Field of Classification Search
CPC .......... G06K 9/00342; G06K 9/00362; G06K 9/00221; G06K 7/10366; G06K 7/10306; H04B 1/1036; H04B 1/7097; H04B 1/71635; H04B 1/71637; H04L 43/04; H04L 67/12; H04W 4/02
USPC .............................. 455/138, 456.1; 340/10.1
See application file for complete search history.

(56) References Cited

U.S. PATENT DOCUMENTS

| | | | |
|---|---|---|---|
| 5,469,409 A | 11/1995 | Anderson et al. | |
| 5,513,854 A | 5/1996 | Daver | |
| 5,645,077 A | 7/1997 | Foxlin | |
| 5,699,244 A | 12/1997 | Clark et al. | |
| 5,901,172 A | 5/1999 | Fontana et al. | |
| 5,920,287 A | 7/1999 | Belcher et al. | |
| 5,930,741 A | 7/1999 | Kramer | |
| 5,995,046 A | 11/1999 | Belcher et al. | |
| 6,028,626 A | 2/2000 | Aviv | |
| 6,121,926 A | 9/2000 | Belcher et al. | |
| 6,176,837 B1 | 1/2001 | Foxlin | |
| 6,204,813 B1 | 3/2001 | Wadell et al. | |
| 6,366,242 B1 | 4/2002 | Boyd et al. | |
| 6,380,894 B1 | 4/2002 | Boyd et al. | |
| 6,593,885 B2 | 7/2003 | Wisherd et al. | |
| 6,655,582 B2 | 12/2003 | Wohl et al. | |
| 6,710,713 B1 | 3/2004 | Russo | |
| 6,812,884 B2 | 11/2004 | Richley et al. | |
| 6,836,744 B1 | 12/2004 | Asphahani et al. | |
| 6,882,315 B2 | 4/2005 | Richley et al. | |
| 7,009,638 B2 | 3/2006 | Gruber et al. | |
| 7,190,271 B2 | 3/2007 | Boyd et al. | |
| 7,667,604 B2 | 2/2010 | Ebert et al. | |
| 7,671,802 B2 | 3/2010 | Walsh et al. | |
| 7,710,322 B1 | 5/2010 | Ameti et al. | |
| 7,755,541 B2 | 7/2010 | Wisherd et al. | |
| 7,899,006 B2 | 3/2011 | Boyd | |
| 7,969,348 B2 | 6/2011 | Baker et al. | |
| 8,077,981 B2 | 12/2011 | Elangovan et al. | |
| 8,269,835 B2 | 9/2012 | Grigsby et al. | |
| 8,279,051 B2 | 10/2012 | Khan | |
| 8,457,392 B2 | 6/2013 | Cavallaro et al. | |
| 8,568,278 B2 | 10/2013 | Riley et al. | |
| 8,696,458 B2 | 4/2014 | Foxlin et al. | |
| 8,705,671 B2 | 4/2014 | Ameti et al. | |
| 8,775,916 B2 | 7/2014 | Pulsipher et al. | |
| 8,780,204 B2 | 7/2014 | DeAngelis et al. | |
| 8,795,045 B2 | 8/2014 | Sorrells et al. | |
| 8,842,002 B2 | 9/2014 | Rado | |
| 8,989,880 B2 | 3/2015 | Wohl et al. | |
| 9,081,076 B2 | 7/2015 | DeAngelis et al. | |
| 2001/0010541 A1 | 8/2001 | Fernandez et al. | |
| 2001/0030625 A1 | 10/2001 | Doles et al. | |
| 2002/0004398 A1 | 1/2002 | Ogino et al. | |
| 2002/0041284 A1 | 4/2002 | Konishi et al. | |
| 2002/0114493 A1 | 8/2002 | McNitt et al. | |
| 2002/0116147 A1 | 8/2002 | Vock et al. | |
| 2002/0135479 A1 | 9/2002 | Belcher et al. | |
| 2003/0090387 A1 | 5/2003 | Lestienne et al. | |
| 2003/0095186 A1 | 5/2003 | Aman et al. | |
| 2003/0128100 A1 | 7/2003 | Burkhardt et al. | |
| 2003/0163287 A1 | 8/2003 | Vock et al. | |
| 2003/0227453 A1 | 12/2003 | Beier et al. | |
| 2004/0022227 A1 | 2/2004 | Lynch et al. | |
| 2004/0062216 A1 | 4/2004 | Nicholls et al. | |
| 2004/0108954 A1* | 6/2004 | Richley .................. G01S 5/06 342/387 |
| 2004/0178960 A1 | 9/2004 | Sun | |
| 2004/0249969 A1 | 12/2004 | Price | |
| 2004/0260470 A1 | 12/2004 | Rast | |
| 2004/0260828 A1 | 12/2004 | Price | |
| 2005/0026563 A1 | 2/2005 | Leeper et al. | |
| 2005/0031043 A1 | 2/2005 | Paquelet | |
| 2005/0059998 A1 | 3/2005 | Norte et al. | |
| 2005/0093976 A1 | 5/2005 | Valleriano et al. | |
| 2005/0148281 A1 | 7/2005 | Sanchez-Castro et al. | |
| 2005/0207617 A1 | 9/2005 | Sarnoff | |
| 2006/0067324 A1* | 3/2006 | Kim .................. H04W 76/022 370/395.2 |
| 2006/0139167 A1 | 6/2006 | Davie et al. | |
| 2006/0164213 A1 | 7/2006 | Burghard et al. | |
| 2006/0252476 A1 | 11/2006 | Bahou | |
| 2006/0271912 A1 | 11/2006 | Mickle et al. | |
| 2006/0281061 A1 | 12/2006 | Hightower et al. | |
| 2007/0091292 A1 | 4/2007 | Cho et al. | |
| 2007/0176749 A1 | 8/2007 | Boyd et al. | |
| 2007/0296723 A1 | 12/2007 | Williams | |
| 2008/0065684 A1 | 3/2008 | Zilberman | |
| 2008/0106381 A1 | 5/2008 | Adamec et al. | |
| 2008/0113787 A1* | 5/2008 | Alderucci .............. G06F 21/31 463/29 |
| 2008/0129825 A1 | 6/2008 | DeAngelis et al. | |
| 2008/0186231 A1 | 8/2008 | Aljadeff et al. | |
| 2008/0262885 A1 | 10/2008 | Jain et al. | |
| 2008/0266131 A1 | 10/2008 | Richardson et al. | |
| 2008/0269016 A1 | 10/2008 | Ungari et al. | |
| 2008/0281443 A1 | 11/2008 | Rodgers | |
| 2008/0285805 A1 | 11/2008 | Luinge et al. | |
| 2009/0048044 A1 | 2/2009 | Oleson et al. | |
| 2009/0141736 A1 | 6/2009 | Becker | |
| 2009/0231198 A1 | 9/2009 | Walsh et al. | |
| 2010/0026809 A1 | 2/2010 | Curry | |
| 2010/0045508 A1 | 2/2010 | Ekbal et al. | |

(56) References Cited

U.S. PATENT DOCUMENTS

| | | |
|---|---|---|
| 2010/0054304 A1 | 3/2010 | Barnes et al. |
| 2010/0060452 A1 | 3/2010 | Schuster et al. |
| 2010/0150117 A1 | 6/2010 | Aweya et al. |
| 2010/0228314 A1 | 9/2010 | Goetz |
| 2010/0250305 A1 | 9/2010 | Lee et al. |
| 2010/0278386 A1 | 11/2010 | Hoeflinger |
| 2010/0283630 A1* | 11/2010 | Alonso .................. H04Q 9/00 340/870.11 |
| 2010/0328073 A1 | 12/2010 | Nikitin et al. |
| 2011/0002223 A1 | 1/2011 | Gross |
| 2011/0025847 A1 | 2/2011 | Park et al. |
| 2011/0054782 A1 | 3/2011 | Kaahui |
| 2011/0084806 A1 | 4/2011 | Perkins et al. |
| 2011/0134240 A1 | 6/2011 | Anderson et al. |
| 2011/0140970 A1 | 6/2011 | Fukagawa et al. |
| 2011/0169959 A1 | 7/2011 | DeAngelis et al. |
| 2011/0188513 A1 | 8/2011 | Christoffersson et al. |
| 2011/0195701 A1 | 8/2011 | Cook et al. |
| 2011/0261195 A1 | 10/2011 | Martin et al. |
| 2011/0300905 A1 | 12/2011 | Levi |
| 2011/0320322 A1 | 12/2011 | Roslak et al. |
| 2012/0014278 A1 | 1/2012 | Ameti et al. |
| 2012/0015665 A1 | 1/2012 | Farley et al. |
| 2012/0024516 A1 | 2/2012 | Bhadurt et al. |
| 2012/0042326 A1 | 2/2012 | Jain et al. |
| 2012/0057634 A1 | 3/2012 | Shi et al. |
| 2012/0057640 A1 | 3/2012 | Shi et al. |
| 2012/0065483 A1 | 3/2012 | Chung et al. |
| 2012/0081531 A1 | 4/2012 | DeAngelis et al. |
| 2012/0112904 A1 | 5/2012 | Nagy et al. |
| 2012/0126973 A1* | 5/2012 | DeAngelis ......... A63B 24/0021 340/539.13 |
| 2012/0139708 A1 | 6/2012 | Paradiso et al. |
| 2012/0184878 A1 | 7/2012 | Najafi et al. |
| 2012/0212505 A1 | 8/2012 | Burroughs et al. |
| 2012/0225676 A1 | 9/2012 | Boyd et al. |
| 2012/0246795 A1 | 10/2012 | Scheffler et al. |
| 2012/0268239 A1 | 10/2012 | Ljung et al. |
| 2013/0003860 A1 | 1/2013 | Sasai et al. |
| 2013/0021142 A1 | 1/2013 | Matsui et al. |
| 2013/0021206 A1 | 1/2013 | Hach et al. |
| 2013/0040574 A1 | 2/2013 | Hillyard |
| 2013/0041590 A1 | 2/2013 | Burich et al. |
| 2013/0066448 A1 | 3/2013 | Alonso |
| 2013/0076645 A1 | 3/2013 | Anantha et al. |
| 2013/0096704 A1 | 4/2013 | Case |
| 2013/0138386 A1 | 5/2013 | Jain et al. |
| 2013/0142384 A1 | 6/2013 | Ofek |
| 2013/0257598 A1 | 10/2013 | Kawaguchi et al. |
| 2013/0339156 A1 | 12/2013 | Sanjay et al. |
| 2014/0055588 A1 | 2/2014 | Bangera et al. |
| 2014/0145828 A1 | 5/2014 | Bassan-Eskenazi |
| 2014/0156036 A1 | 6/2014 | Huang |
| 2014/0170607 A1 | 6/2014 | Hsiao et al. |
| 2014/0221137 A1 | 8/2014 | Krysiak et al. |
| 2014/0320660 A1 | 10/2014 | DeAngelis et al. |
| 2014/0361875 A1 | 12/2014 | O'Hagan et al. |
| 2014/0361906 A1 | 12/2014 | Hughes et al. |
| 2014/0364141 A1 | 12/2014 | O'Hagan et al. |
| 2014/0365415 A1 | 12/2014 | Stelfox et al. |
| 2015/0002272 A1 | 1/2015 | Alonso et al. |
| 2015/0057981 A1 | 2/2015 | Gross |
| 2015/0085111 A1 | 3/2015 | Lavery |
| 2015/0097653 A1 | 4/2015 | Gibbs et al. |
| 2015/0355311 A1 | 12/2015 | O'Hagan et al. |
| 2015/0358852 A1 | 12/2015 | Richley et al. |
| 2015/0360133 A1 | 12/2015 | MacCallum et al. |
| 2015/0375041 A1 | 12/2015 | Richley et al. |
| 2015/0375083 A1 | 12/2015 | Stelfox et al. |
| 2015/0378002 A1 | 12/2015 | Hughes et al. |
| 2015/0379387 A1 | 12/2015 | Richley |
| 2016/0097837 A1 | 4/2016 | Richley et al. |

FOREIGN PATENT DOCUMENTS

| | | |
|---|---|---|
| EP | 1503513 A1 | 2/2005 |
| EP | 2474939 A1 | 11/2012 |
| WO | WO-9805977 A1 | 2/1998 |
| WO | WO 99/61936 A1 | 12/1999 |
| WO | WO 0108417 | 2/2001 |
| WO | WO 2006/022548 | 3/2006 |
| WO | WO-2010/083943 A1 | 7/2010 |
| WO | WO 2015/051813 A1 | 4/2014 |
| WO | WO 2014197600 | 12/2014 |

OTHER PUBLICATIONS

Complaint before the United States District Court of Massachusetts, Civil Action No. 1:15-cv-12297, *Lynx System Developers, Inc. et al. v. Zebra Enterprise Solutions Corporation et al.*, filed Jun. 10, 2015.

Swedberg, Claire, "USDA Researchers Develop System to Track Livestock Feeding Behavior Unobtrusively", RFID Journal, Jul. 18, 2013.

International Search Report and Written Opinion from International Application No. PCT/US2014/040881 dated Nov. 4, 2014.

International Search Report and Written Opinion from International Application No. PCT/US2014/041062 dated Oct. 1, 2014.

International Search Report and Written Opinion from International Application No. PCT/US2014/040947 dated Oct. 9, 2014.

Fontana, R.J., Richley, E., Barney, J., "Commercialization of an Ultra Wideband Precision Asset Location System," *2003 IEEE Conference on Ultra Wideband Systems and Technologies*, Nov. 16-19, 2003.

Gueziec, A., "Tracking Pitches for Broadcast Television," *Computer*, Aug. 7, 2002.

CattleLog Pro, *eMerge Interactive, Inc.*, Sebastian, FL, 2004.

Marchant, J., Secure Animal Identification and Source Verification, *JM Communications*, UK, 2002.

"A Guide to Using NLIS Approved Ear Tags and Rumen Boluses," National Livestock Identification Scheme, *Meat & Livestock Australia Limited*, North Sydney, Australia, May 2003.

King, L., "NAIS Cattle ID Pilot Projects Not Needed, Since Proven Advanced Technology Already Exists," *ScoringSystem, Inc.*, Sarasota, FL, Dec. 27, 2005. (www.prweb.com/releases/2005/12prweb325888.htm).

"RFID in the Australian Meat and Livestock Industry," Allflex Australia Pty Ltd,Capalaba, QLD (AU), *Data Capture Suppliers Guide*, 2003-2004.

International Search Report and Written Opinion for International Application No. PCT/IB2015/054099 dated Dec. 9, 2015.

Complaint before the United States District Court of Massachusetts, Civil Action No. 1:15-cv-12297, *Lynx System Developers, Inc. et al. V. Zebra Enterprise Solutions Corporation et al.*, filed Mar. 23, 2016.

Defendant's Answer to Complaint before the United States District Court of Massachusetts, Civil Action No. 1:15-cv-12297, *Lynx System Developers, Inc. et al. V. Zebra Enterprise Solutions Corporation et al.*, filed Apr. 6, 2016.

Invitation to Pay Additional Fees/Partial International Search Report for PCT/IB2015/054099 dated Oct. 6, 2015.

Swedberg, C., "N.J. Company Seeks to Market Passive Sensor RFID Tags", RFID Journal, Jun. 14, 2011, <http://www.rfidjournal.com/articles/pdf?8527>.

U.S. Appl. No. 14/296,703, filed Jun. 5, 2014; In re: Alonso et al., entitle Method and Apparatus for Associating Radio Frequency Identification Tags with Participants.

U.S. Appl. No. 61/895,548, filed Oct. 25, 2013, In re: Alonso et al., entitled "Method, Apparatus, and Computer Program Product for Collecting Sporting Event Data Based on Real Time Data for Proximity and Movement of Objects".

International Search Report and Written Opinion for International Application No. PCT/IB2015/059264 dated Feb. 10, 2016.

Jinyun Zhang et al., "UWB Systems for Wireless Sensor Networks", Proceedings of the IEEE, IEEE. New York, US, vol. 97, No. 2, Feb. 1, 2009 (Feb. 1, 2009), pp. 313-331.

(56) References Cited

OTHER PUBLICATIONS

International Search Report and Written Opinion for International Application No. PCT/US2015/034267 dated Sep. 25, 2015.
International Search Report and Written Opinion for International Application No. PCT/IB2015/054103 dated Aug. 14, 2015.
Cheong, P. et al., "Synchronization, TOA and Position Estimation for Low-Complexity LDR UWB Devices", Ultra-Wideband, 2005 IEEE International Conference, Zurich, Switzerland Sep. 5-8, 2005, Piscataway, NJ, USA, IEEE, Sep. 5, 2005, pp. 480-484.
International Search Report and Written Opinion for International Application No. PCT/IB2015/054213 dated Aug. 6, 2015.
Wang, Y. et al., "An Algorithmic and Systematic Approach from Improving Robustness of TOA-Based Localization", 2013 IEEE 10th International Conference on High Performance Computing and Communications & 2013 IEEE, Nov. 13, 2013, pp. 2066-2073.
Guvenc, I. et al., "A Survey on TOA Based Wireless Localization and NLOA Mitigation Techniques", IEEE Communications Surveys, IEEE, New York, NY, US, vol. 11, No. 3, Oct. 1, 2009, pp. 107-124.
International Search Report and Written Opinion for International Application PCT/IB2015/054102 dated Nov. 4, 2015.
"Seattleite wins top prize in Microsoft's Super Bowl tech Contest", San Francisco AP, Komonews.com, Feb. 6, 2016. <http://komonews.com/news/local/seattleite-wins-top-prize-in-microsofts-super-bowl-tech-contest>.
Bahle et al., "I See You: How to Improve Wearable Activity Recognition by Leveraging Information from Environmental Cameras," Pervasive Computing and Communications Workshops, IEEE International Conference, (Mar. 18-22, 2013).
Teixeira et al., "Tasking Networked CCTV Cameras and Mobile Phones to Identify and Localize Multiple People," Ubicomp '10 Proceedings of the 12th ACM International Conference on Ubiquitous Computing, pp. 213-222 (Sep. 26-29, 2010).
International Search Report and Written Opinion for International Application No. PCT/US2016/035614 dated Sep. 15, 2016.
Zhu et al., "A Real-Time Articulated Human Motion Tracking Using Tri-Axis Inertial/Magnetic Sensors Package," IEEE Transactions on Neural Systems and Rehabilitation Engineering, vol. 12, No. 2, Jun. 2004, pp. 295-302.
European Search Report for European Patent Application No. 14806811.7 dated Dec. 9, 2016.

* cited by examiner

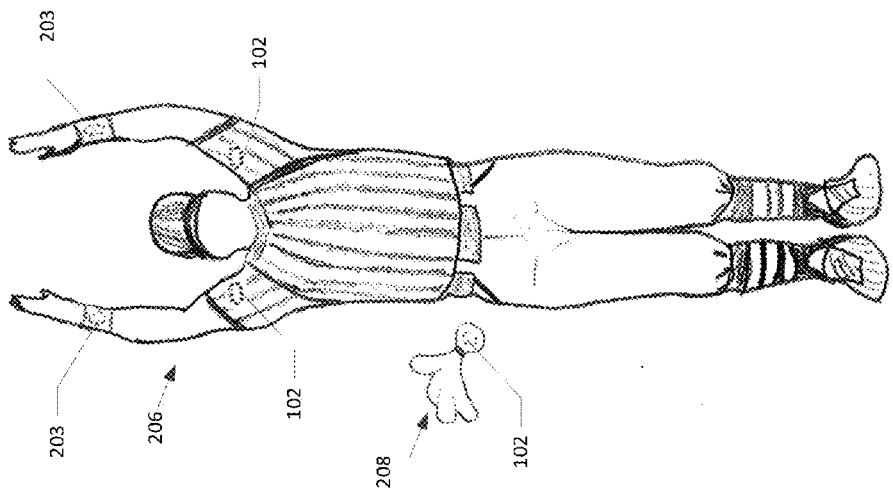
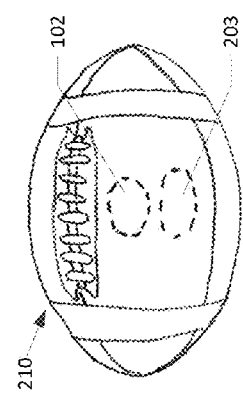
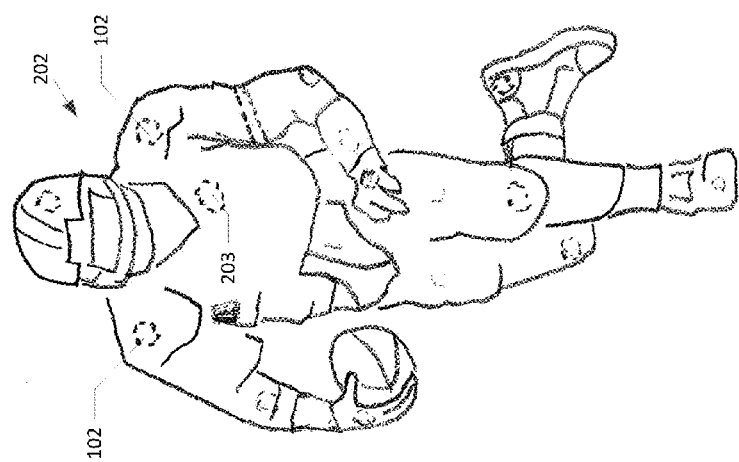
Figure 2B
Figure 2C
Figure 2A

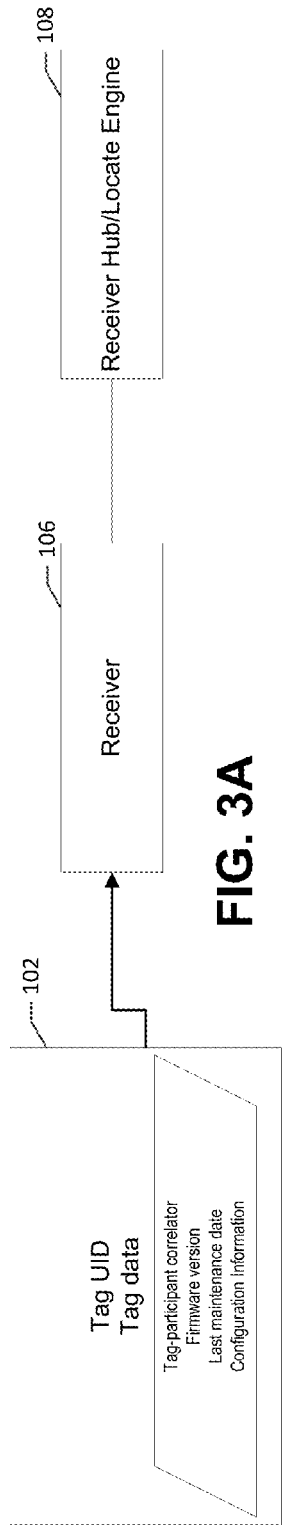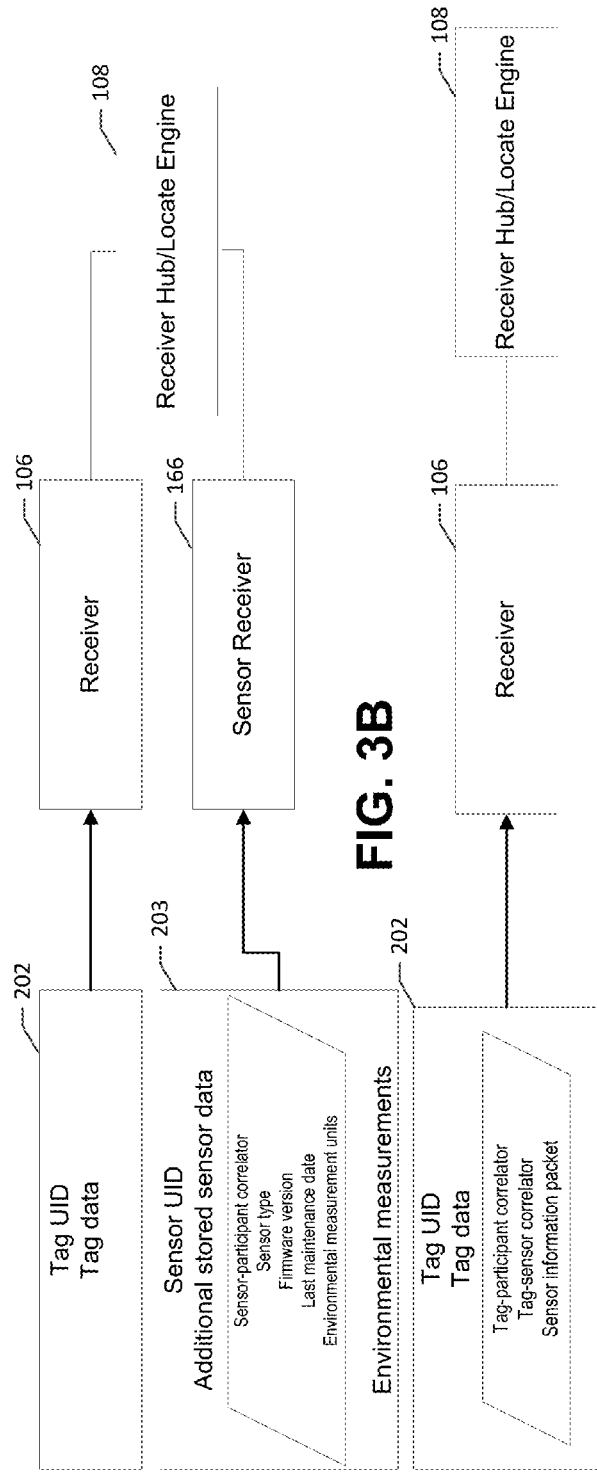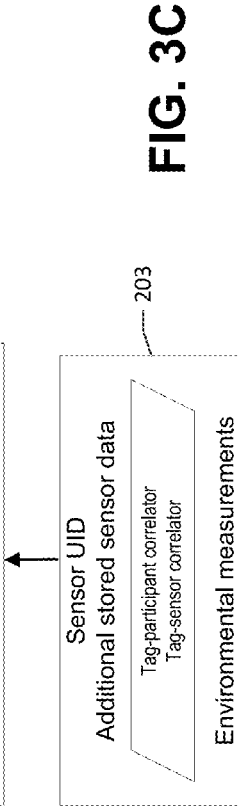

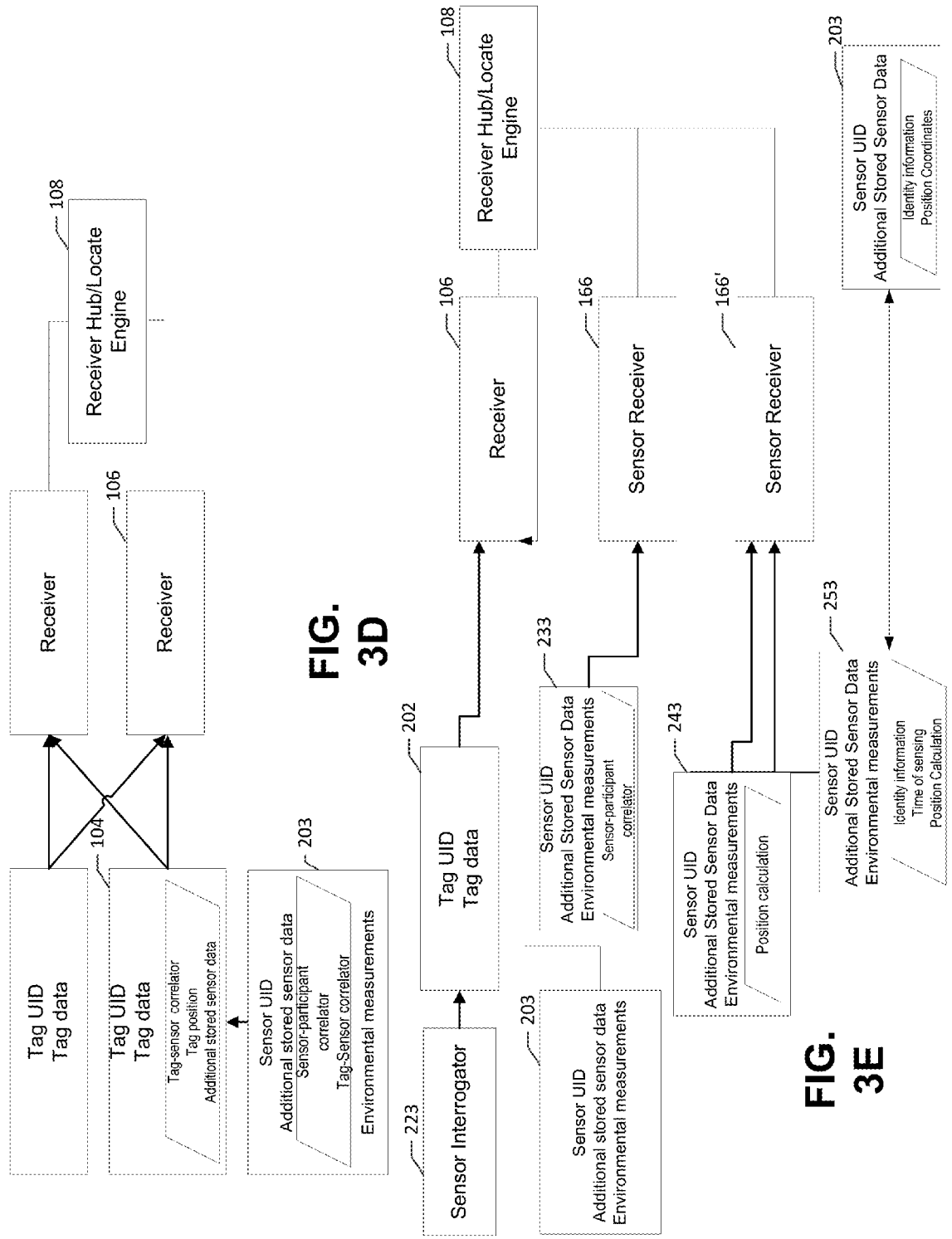

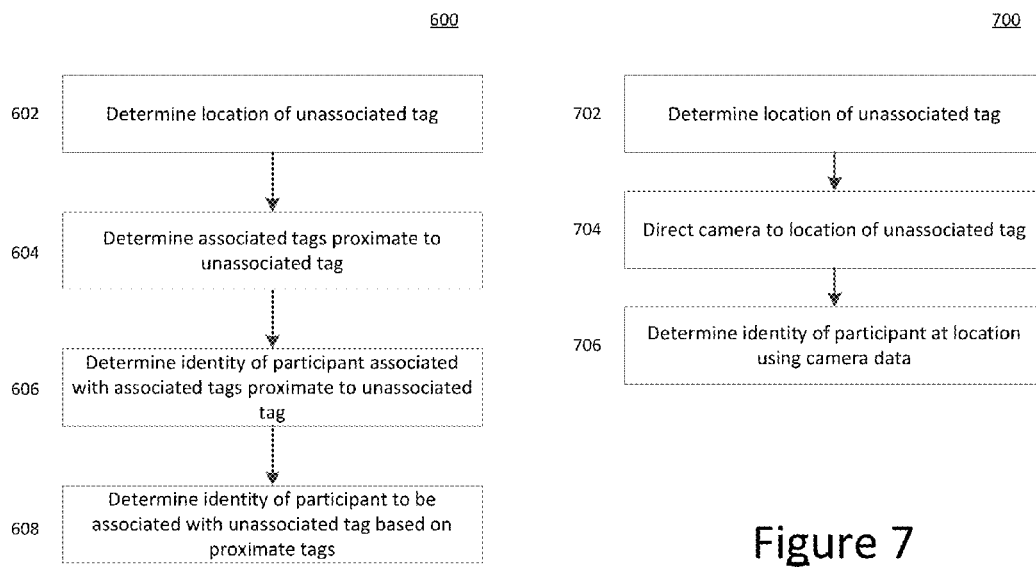
Figure 6
Figure 7
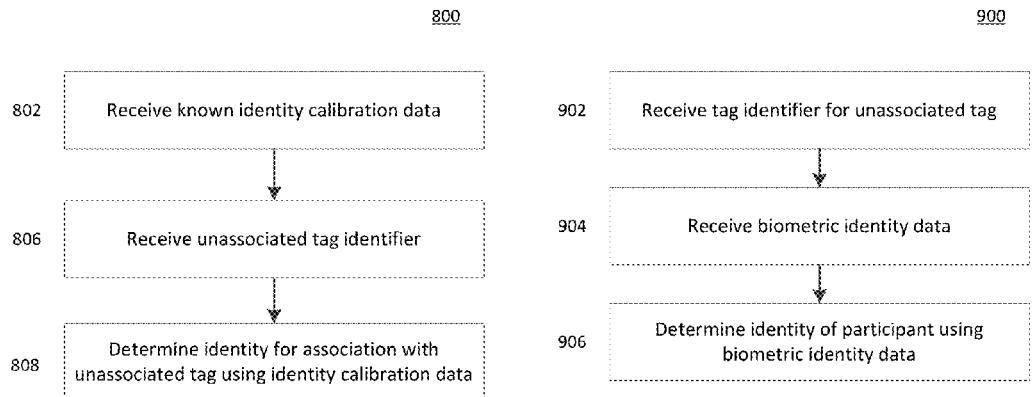
Figure 8
Figure 9

METHOD AND APPARATUS FOR ASSOCIATING RADIO FREQUENCY IDENTIFICATION TAGS WITH PARTICIPANTS

CROSS-REFERENCE TO RELATED APPLICATIONS

This application claims priority to U.S. Provisional Application No. 61/831,990, filed Jun. 6, 2013, the entire contents of which are incorporated herein by reference.

FIELD

Embodiments discussed herein are related to radio frequency locating and, more particularly, to systems, methods, apparatuses, computer readable media and other means for associating radio frequency identification tags with particular participants.

BACKGROUND

Determining associations between particular radio frequency identification tags and particular physical entities is difficult in an environment containing many such tags. Limitations of Radio Frequency Identification (RFID) technology may cause difficulty in identifying precisely which tag corresponds to which participant. A number of deficiencies and problems associated with radio frequency location identification and the association of location tags with particular participants are identified herein. Through applied effort, ingenuity, and innovation, exemplary solutions to many of these identified problems are embodied by the present invention, which is described in detail below.

BRIEF SUMMARY

Systems, methods, apparatuses, and computer readable media are disclosed for associating radio frequency tags with particular participants for use in a location detection system.

Embodiments may include a method for associating a participant with a radio frequency location tag ("RF location tag"). The method may include determining an unassociated tag to be associated with the participant, receiving sensor derived data from one or more sensors, determining an identity of the particular participant using the sensor derived data, and associating the identity of the particular participant with the unassociated tag.

In some embodiments, the sensor derived data may be visual data. At least one of the sensors may be a camera. The method may also include determining a location of the unassociated tag using a radio frequency locating system, directing the camera to the location of the unassociated tag, and capturing the visual data. The visual data may correspond to the location of the unassociated tag. The method may also include deriving the identity of the participant from the visual data.

In some embodiments, the sensor derived data may be biometric data, and at least one of the sensors is a biometric scanner. The method may also include receiving the biometric data from the biometric scanner. The biometric data may be obtained from the particular participant. The method may also include determining the identity of the particular participant using the biometric data. The unassociated tag may include an ultra-wideband (UWB) transmitter. The UWB transmitter may be configured to transmit a plurality of time of arrival (TOA) timing pulses. The UWB transmitter may also be configured to transmit an information packet comprising 112 bits.

Embodiments may also include another method for associating a participant with a radio frequency identification (RFID) tag. This method may include determining an unassociated tag to be associated with the participant, determining a location of the unassociated tag, determining at least one associated tag proximate to the location of the unassociated tag, determining an identity of the particular participant based on an identity associated with the at least one associated tag, and associating the identity of the particular participant with the unassociated tag. In some embodiments, the method may further include identifying a plurality of associated tags proximate to the unassociated tag, determining a plurality of participants corresponding to the plurality of associated tags, constraining a possible set of participants used for identifying the particular participant using the plurality of participants, and determining the identity of the particular participant from the possible set of participants. The identity of the particular participant may be determined by identifying one of the plurality of participants that fails to provide data from at least one of a set of associated RF location tags associated with the one of the plurality of participants.

Embodiments may also include yet another method for associating a participant with a radio frequency identification (RFID) tag. This method may include receiving known identity calibration data, determining a participant identity based on the known identity calibration data, receiving an identifier for an unassociated RF location tag, and associating the unassociated RF location tag with the participant identity. The known identity calibration data may specify an order of participants. The known identity calibration data may be biometric data.

Embodiments may also provide an apparatus for associating a participant with a radio frequency identification (RFID) tag. The apparatus may include a processor configured to cause the apparatus to at least determine an unassociated tag to be associated with the participant, receive sensor derived data from one or more sensors coupled to the apparatus, determine an identity of the particular participant using the sensor derived data, and associate the identity of the particular participant with the unassociated tag.

In some embodiments, the sensor derived data may be visual data. At least one of the sensors may be a camera. The processor may be further configured to cause the apparatus to determine a location of the unassociated tag using a radio frequency locating system, to direct the camera to the location of the unassociated tag, to capture the visual data, the visual data corresponding to the location of the unassociated tag, and to derive the identity of the participant from the visual data.

In some embodiments, the sensor derived data may be biometric data. At least one of the sensors may be a biometric scanner. The processor may be further configured to cause the apparatus to receive the biometric data from the biometric scanner. The biometric data may be obtained from the particular participant. The processor may be further configured to determine the identity of the particular participant using the biometric data.

The unassociated tag may include an ultra-wideband (UWB) transmitter. The UWB transmitter may be configured to transmit a plurality of time of arrival (TOA) timing pulses. The UWB transmitter may also be configured to transmit an information packet comprising 112 bits.

Embodiments may also provide an another apparatus for associating a participant with a radio frequency identification (RFID) tag. The apparatus may include a processor configured to cause the apparatus at least to determine an unassociated tag to be associated with the participant, to determine a location of the unassociated tag, to determine at least one associated tag proximate to the location of the unassociated tag, to determine an identity of the particular participant based on an identity associated with the at least one associated tag, and to associate the identity of the particular participant with the unassociated tag. The processor may also be configured to cause the apparatus to identify a plurality of associated tags proximate to the unassociated tag, to determine a plurality of participants corresponding to the plurality of associated tags, to constrain a possible set of participants used for identifying the particular participant using the plurality of participants, and to determine the identity of the particular participant from the possible set of participants. The identity of the particular participant may be determined by identifying one of the plurality of participants that fails to provide data from at least one of a set of associated RF location tags associated with the one of the plurality of participants.

Embodiments may also include another an apparatus for associating a participant with a radio frequency identification (RFID) tag. The apparatus may include a processor configured to cause the apparatus at least to receive known identity calibration data, to determine a participant identity based on the known identity calibration data, to receive an identifier for an unassociated RF location tag, and to associate the unassociated RF location tag with the participant identity. The known identity calibration data may specify an order of participants. The known identity calibration data may be biometric data.

Embodiments may also include a computer program product comprising at least one non-transitory computer readable storage medium. The non-transitory computer readable storage medium may store instructions that, when executed by a processor, cause the processor to configure an apparatus. The processor may configure the apparatus at least to determine an unassociated tag to be associated with the participant, to receive sensor derived data from one or more sensors coupled to the apparatus, to determine an identity of the particular participant using the sensor derived data, and to associate the identity of the particular participant with the unassociated tag. In some embodiments, the unassociated tag includes an ultra-wideband (UWB) transmitter. The UWB transmitter may be configured to transmit a plurality of time of arrival (TOA) timing pulses. The UWB transmitter may be configured to transmit an information packet comprising 112 bits.

In some embodiments, the sensor derived data may be visual data and at least one of the sensors may be a camera. The instructions may further cause the processor to configure the apparatus at least to determine a location of the unassociated tag using a radio frequency locating system, to direct the camera to the location of the unassociated tag, and to capture the visual data. The visual data may correspond to the location of the unassociated tag. The instructions may further cause the processor to configure the apparatus to derive the identity of the participant from the visual data.

The sensor derived data may be biometric data, and at least one of the sensors may be a biometric scanner. The instructions may further cause the processor to configure the apparatus at least to receive the biometric data from the biometric scanner. The biometric data may be obtained from the particular participant. The instructions may further cause the processor to configure the apparatus to determine the identity of the particular participant using the biometric data.

Embodiments may include another computer program product including at least one non-transitory computer readable storage medium. The non-transitory computer readable storage medium may store instructions that, when executed by a processor, cause the processor to configure an apparatus. The apparatus may be configured by the processor at least to determine an unassociated tag to be associated with the participant, to determine a location of the unassociated tag, to determine at least one associated tag proximate to the location of the unassociated tag, to determine an identity of the particular participant based on an identity associated with the at least one associated tag, and to associate the identity of the particular participant with the unassociated tag. The instructions may further cause the processor to configure the apparatus at least to identify a plurality of associated tags proximate to the unassociated tag, to determine a plurality of participants corresponding to the plurality of associated tags, to constrain a possible set of participants used for identifying the particular participant using the plurality of participants, and to determine the identity of the particular participant from the possible set of participants. The identity of the particular participant may be determined by identifying one of the plurality of participants that fails to provide data from at least one of a set of associated RF location tags associated with the one of the plurality of participants.

Embodiments may also include yet another computer program product including at least one non-transitory computer readable storage medium. The non-transitory computer readable storage medium may store instructions that, when executed by a processor, cause the processor to configure an apparatus. The apparatus may be configured at least to receive known identity calibration data, to determine a participant identity based on the known identity calibration data, to receive an identifier for an unassociated RF location tag, and to associate the unassociated RF location tag with the participant identity. The known identity calibration data may specify an order of participants. The known identity calibration data may be biometric data.

Embodiments may further include a method for associating a participant with a radio frequency (RF) location tag. The method includes transmitting an activation signal within a designated zone. The activation signal causes the RF location tag to activate upon receipt and transmit an activation notification. The method further includes receiving the activation notification from the RF location tag, determining, using a processor, a participant identity within the designated zone using information received from one or more sensors, and associating the RF location tag with the participant identity. The information may include visual data and the one or more sensors comprise a camera. The visual data may include an image of a player jersey. In some embodiments, the method further includes determining an orientation of the RF location tag using the information received from the one or more sensors.

Embodiments may also include an apparatus for associating a participant with a radio frequency (RF) location tag. The apparatus includes a processor configured to cause the apparatus to at least transmit an activation signal within a designated zone. The activation signal causes the RF location tag to activate upon receipt and transmit an activation notification. The processor may further configure the apparatus to receive the activation notification from the RF location tag, to determine a participant identity within the designated zone using information received from one or more sensors, and to associate the RF location tag with the participant identity. The information may include visual data and the one or more sensors comprise a camera. The visual data may include an image of a player jersey. The apparatus may be further configured to determine an orientation of the RF location tag using the information received from the one or more sensors.

Embodiments may also include a computer program product comprising at least one non-transitory computer readable storage medium. The non-transitory computer readable storage medium stores instructions that, when executed by a processor, cause the processor to configure an apparatus to at least transmit an activation signal within a designated zone. The activation signal causes the RF location tag to activate upon receipt and transmit an activation notification. The instructions further cause the processor to configure the apparatus to receive the activation notification from the RF location tag, determine a participant identity within the designated zone using information received from one or more sensors, and associate the RF location tag with the participant identity. The information may include visual data and the one or more sensors comprise a camera. The visual data may include an image of a player jersey. The instructions may further cause the processor to configure the apparatus to determine an orientation of the RF location tag using the information received from the one or more sensors.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

FIG. 1 illustrates an exemplary environment using a radio frequency locating system for associating tags with participants in accordance with some embodiments of the present invention;

FIGS. 2A-C illustrate some exemplary participants carrying tags and sensors that may provide for association of tags with participants in accordance with some embodiments of the present invention;

FIGS. 3A-3E illustrate schematic block diagrams of various exemplary tags and sensors communicating with receivers and sensor receivers in accordance with various embodiments of the invention;

Figure 11:
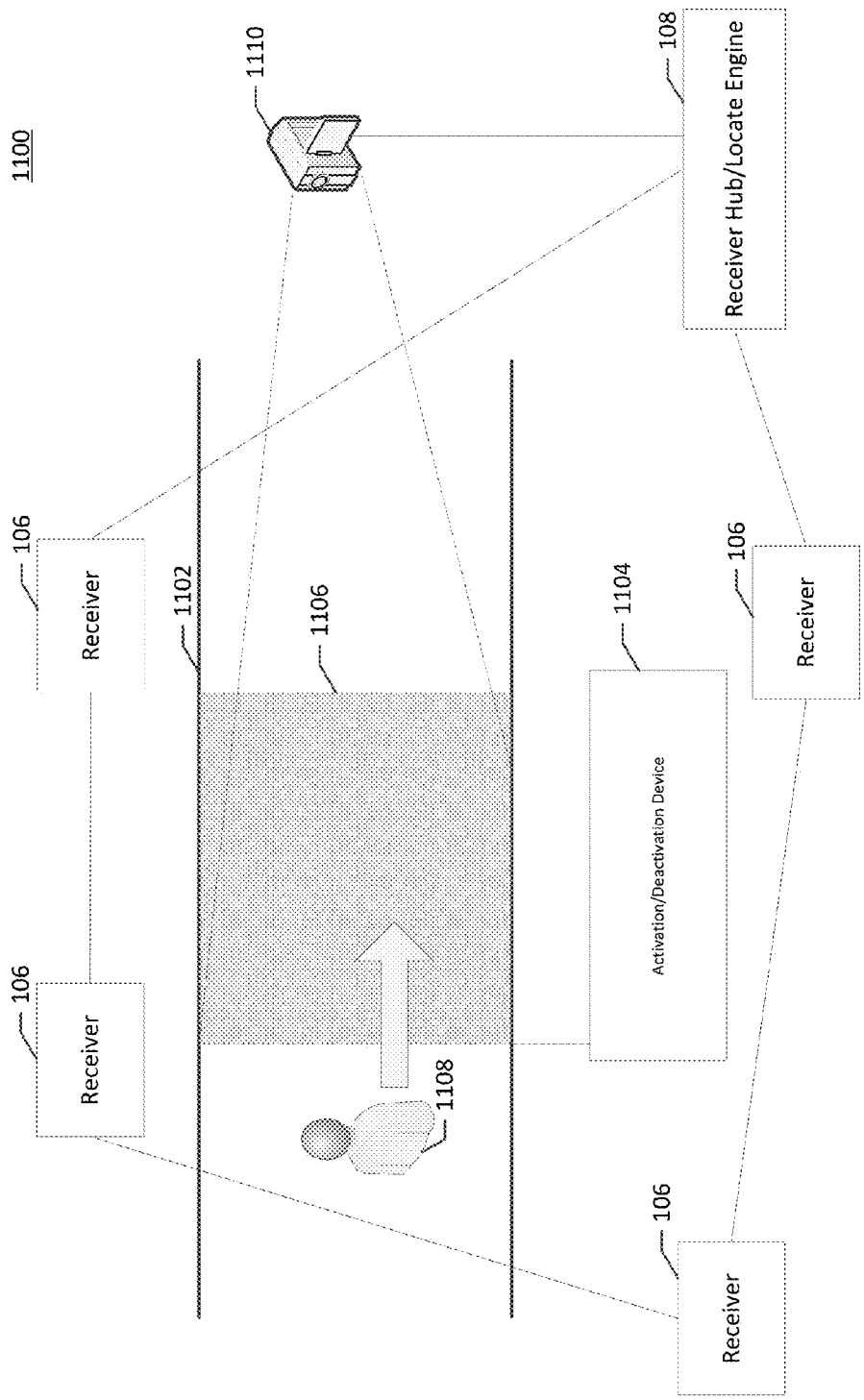
Figure 12:
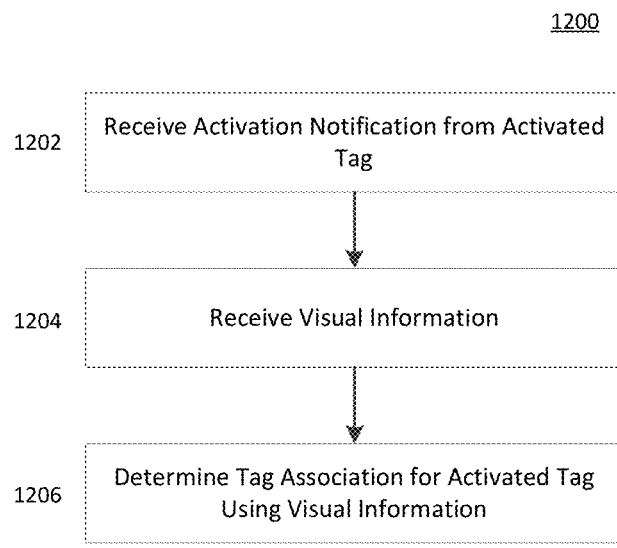
Figure 13:
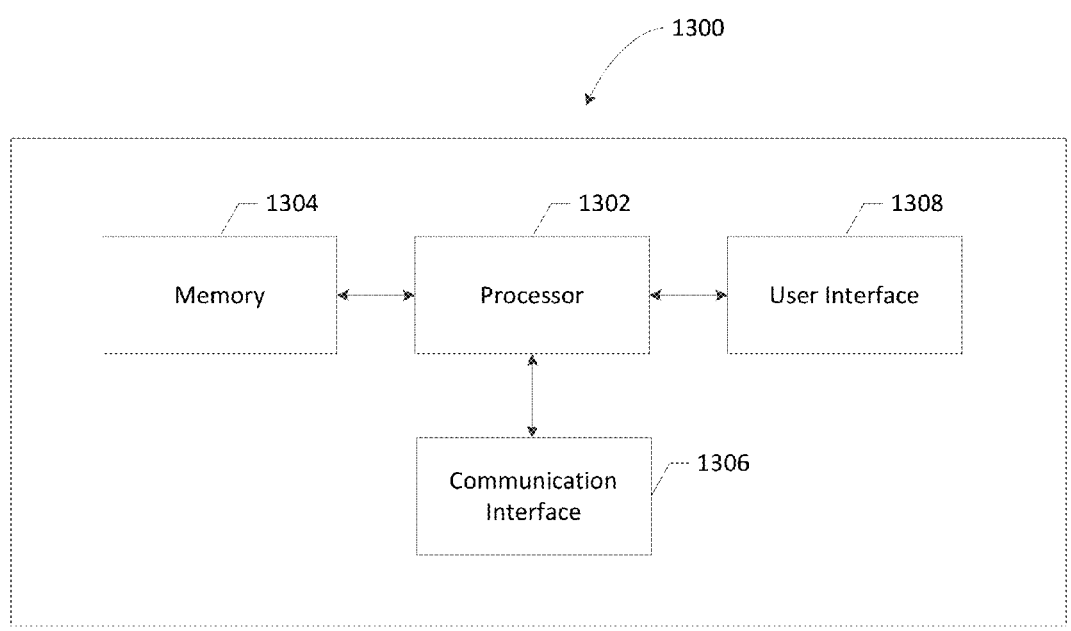

FIGS. 5-10 provide flowcharts of some exemplary processes that may be used to associate a tag with a participant in accordance with some embodiments of the present invention;

FIG. 11 illustrates an exemplary system for automatically activating and/or deactivating tags in accordance with some embodiments of the present invention;

FIG. 12 provides a flowchart of an exemplary process that may be used to automatically activate and/or register a tag in accordance with some embodiments of the present invention; and FIG. 13 illustrates a block diagram of components that may be included in devices for associating a tag with a participant in accordance with some embodiments of the present invention.

DETAILED DESCRIPTION

The present invention now will be described more fully hereinafter with reference to the accompanying drawings, in which some, but not all embodiments of the inventions are shown. Indeed, the invention may be embodied in many different forms and should not be construed as limited to the embodiments set forth herein; rather, these embodiments are provided so that this disclosure will satisfy applicable legal requirements. Like numbers refer to like elements throughout.

Overview

Existing systems that identify the location of entities using Radio Frequency Identification (RFID) tags may include the use of multiple tags per participant to establish an accurate location of the participant. However, in order to track the participant using those tags, the tags may first be registered with that particular participant, and then activated to begin tracking the participant. For the purposes of this application, the term "associate" or "association" when described in relation to associating a tag with a participant may encompass the process of registering and/or activating the tag with respect to the particular participant. Existing techniques for associating tags with particular entities may be inadequate in environments with many active tags due to range precision limitations of devices used to program the tags. Furthermore, it would be advantageous to simplify the process of selecting a particular participant with which to associate the tag to increase efficiency in reassignment, replacement, maintenance, and initial association of tags with particular entities.

For example, in a professional sports environment, it may not be feasible to ask a player to switch out their equipment during a game due to a malfunctioning RF location tag. As players congregate on the sidelines, it may be difficult to associate a particular tag with a particular player due to cross-talk and interference generated from RF location tags associated with all of the players in close proximity to one another and other electronic equipment, radios, cameras, and phones. Players may be reluctant to leave the game to separate themselves from the interference or to replace a malfunctioning tag. As such, example embodiments advantageously provide for systems and methods that reduce the complexity of the process of associating a particular RF location tag or set of tags with a particular participant.

Additionally, tags may be selectively activated and deactivated. For example, tags may be associated with power sources, such as batteries. When a tag is activated, the tag may begin to consume battery power. However, the use of battery power in this manner may introduce certain tradeoffs. Longer tag life may require the use of larger batteries, increasing the size and weight of the tag. By deactivating tags that are not in use, battery life may be conserved, allowing for the use of smaller batteries and extending the life of existing batteries. However, efficient activation and deactivation may be difficult due to the need for the tag to be in close proximity with a device capable of performing the activation or deactivation. Enclosed environments, such as a locker room, may not be capable of supporting additional personnel to provide for tag activation and deactivation.

The term "participant" should be understood to include any physical item or person to which a particular RF location tag or set of tags may be associated. For example, the term "participant" as used herein may refer to players, player equipment (e.g., a set of shoulder pads, a wristband, a jersey, or a helmet), officials, game related objects (e.g., a ball, penalty marker, line of scrimmage and yard to gain markers), and any other movable object proximate a monitored area such as a field of play.

Embodiments of the present invention are directed to methods, systems, apparatuses, and computer readable storage media for associating particular RF location tags with particular participants. Embodiments of the present invention may provide for automatic determination of participant identities and association of the entity identities with particular RF location tags as described in detail below. Embodiments of the present invention may provide for automated data collection with reduced errors, as well as providing additional statistics that may not be available with current systems.

Embodiments of the present invention may allow for sensor derived data to be provided for use in the association of one or more RF location tags with a particular participant. For example, sensor derived data may be received from, without limitation, cameras, biometric readers (e.g., fingerprint readers, retinal scanners, facial recognition scanners, and the like), barcode readers, RFID receivers, near field communications (NFC) readers, global positioning system (GPS) receivers, or the like. The identity of a participant may be determined using the sensor derived data, and an RF location tag may be associated with the identified participant.

Embodiments of the present invention are illustrated in the appended figures and description below in relation to the sport of American football. However, as will be apparent to one of ordinary skill in the art in view of this disclosure, the inventive concepts herein described are not limited to football and may be applied to various other applications including, without limitation, other sports such as baseball, basketball, golf, hockey, soccer, and the like.

Example RF Locating System Architecture

Figure 1:
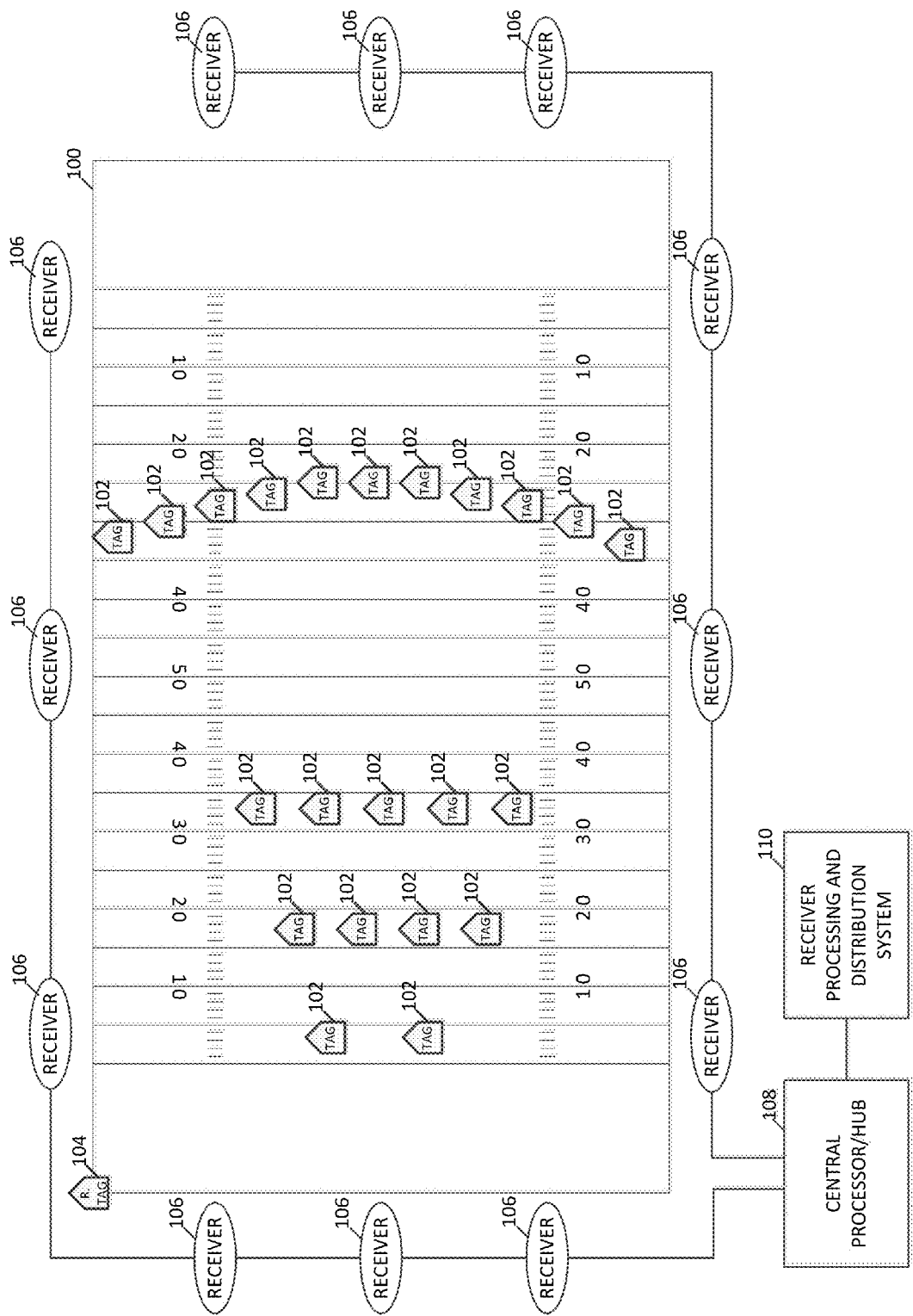

FIG. 1 illustrates an exemplary locating system 100 useful for calculating a location by an accumulation of position data or time of arrivals (TOAs) at a central processor/Hub 108, whereby the TOAs represent a relative time of flight (TOF) from RTLS tags 102 as recorded at each receiver 106 (e.g., UWB reader, etc.). A timing reference clock is used, in some examples, such that at least a subset of the receivers 106 may be synchronized in frequency, whereby the relative TOA data associated with each of the RTLS tags 102 may be registered by a counter associated with at least a subset of the receivers 106. In some examples, a reference tag 104, preferably a UWB transmitter, positioned at known coordinates, is used to determine a phase offset between the counters associated with at least a subset of the of the receivers 106. The RTLS tags 102 and the reference tags 104 reside in an active RTLS field. The systems described herein may be referred to as either "multilateration" or "geolocation" systems, terms that refer to the process of locating a signal source by solving an error minimization function of a location estimate determined by the difference in time of arrival (DTOA) between TOA signals received at multiple receivers 106.

In some examples, the system comprising at least the tags 102 and the receivers 106 is configured to provide two dimensional and/or three dimensional precision localization (e.g., subfoot resolutions), even in the presence of multipath interference, due in part to the use of short nanosecond duration pulses whose TOF can be accurately determined using detection circuitry, such as in the receivers 106, which can trigger on the leading edge of a received waveform. In some examples, this short pulse characteristic allows necessary data to be conveyed by the system at a higher peak power, but lower average power levels, than a wireless system configured for high data rate communications, yet still operate within local regulatory requirements.

In some examples, to provide a preferred performance level while complying with the overlap of regulatory restrictions (e.g. FCC and ETSI regulations), the tags 102 may operate with an instantaneous −3 dB bandwidth of approximately 400 MHz and an average transmission below 187 pulses in a 1 msec interval, provided that the packet rate is sufficiently low. In such examples, the predicted maximum range of the system, operating with a center frequency of 6.55 GHz, is roughly 200 meters in instances in which a 12 dBi directional antenna is used at the receiver, but the projected range will depend, in other examples, upon receiver antenna gain. Alternatively or additionally, the range of the system allows for one or more tags 102 to be detected with one or more receivers positioned throughout a football stadium used in a professional football context. Such a configuration advantageously satisfies constraints applied by regulatory bodies related to peak and average power densities (e.g., effective isotropic radiated power density ("EIRP")), while still optimizing system performance related to range and interference. In further examples, tag transmissions with a −3 dB bandwidth of approximately 400 MHz yields, in some examples, an instantaneous pulse width of roughly 2 nanoseconds that enables a location resolution to better than 30 centimeters.

Referring again to FIG. 1, the object to be located has an attached tag 102, preferably a tag having a UWB transmitter, that transmits a burst (e.g., multiple pulses at a 1 Mb/s burst rate, such as 112 bits of On-Off keying (OOK) at a rate of 1 Mb/s), and optionally, a burst comprising an information packet utilizing OOK that may include, but is not limited to, ID information, a sequential burst count or other desired information for object or personnel identification, inventory control, etc. In some examples, the sequential burst count (e.g., a packet sequence number) from each tag 102 may be advantageously provided in order to permit, at a Central Processor/Hub 108, correlation of TOA measurement data from various receivers 106.

In some examples, the tag 102 may employ UWB waveforms (e.g., low data rate waveforms) to achieve extremely fine resolution because of their extremely short pulse (i.e., sub-nanosecond to nanosecond, such as a 2 nsec (1 nsec up and 1 nsec down)) durations. As such, the information packet may be of a short length (e.g. 112 bits of OOK at a rate of 1 Mb/sec, in some example embodiments), that advantageously enables a higher packet rate. If each information packet is unique, a higher packet rate results in a higher data rate; if each information packet is transmitted repeatedly, the higher packet rate results in a higher packet repetition rate. In some examples, higher packet repetition rate (e.g., 12 Hz) and/or higher data rates (e.g., 1 Mb/sec, 2 Mb/sec or the like) for each tag may result in larger datasets for filtering to achieve a more accurate location estimate. Alternatively or additionally, in some examples, the shorter length of the information packets, in conjunction with other packet rate, data rates and other system requirements, may also result in a longer battery life (e.g., 7 years battery life at a transmission rate of 1 Hz with a 300 mAh cell, in some present embodiments).

Tag signals may be received at a receiver directly from RTLS tags, or may be received after being reflected en route. Reflected signals travel a longer path from the RTLS tag to the receiver than would a direct signal, and are thus received later than the corresponding direct signal. This delay is known as an echo delay or multipath delay. If reflected signals are sufficiently strong enough to be detected by the receiver, they can corrupt a data transmission through inter-symbol interference. In some examples, the tag 102 may employ UWB waveforms to achieve extremely fine resolution because of their extremely short pulse (e.g., 2 nsec) durations. Furthermore, signals may comprise short information packets (e.g., 112 bits of OOK) at a somewhat high burst data rate (1 Mb/sec, in some example embodiments), that advantageously enable packet durations to be brief (e.g. 112 microsec) while allowing inter-pulse times (e.g., 998 nsec) sufficiently longer than expected echo delays, avoiding data corruption.

Reflected signals can be expected to become weaker as delay increases due to more reflections and the longer distances traveled. Thus, beyond some value of inter-pulse time (e.g., 998 nsec), corresponding to some path length difference (e.g., 299.4 m.), there will be no advantage to further increases in inter-pulse time (and, hence lowering of burst data rate) for any given level of transmit power. In this manner, minimization of packet duration allows the battery life of a tag to be maximized, since its digital circuitry need only be active for a brief time. It will be understood that different environments can have different expected echo delays, so that different burst data rates and, hence, packet durations, may be appropriate in different situations depending on the environment.

Minimization of the packet duration also allows a tag to transmit more packets in a given time period, although in practice, regulatory average EIRP limits may often provide an overriding constraint. However, brief packet duration also reduces the likelihood of packets from multiple tags overlapping in time, causing a data collision. Thus, minimal packet duration allows multiple tags to transmit a higher aggregate number of packets per second, allowing for the largest number of tags to be tracked, or a given number of tags to be tracked at the highest rate.

In one non-limiting example, a data packet length of 112 bits (e.g., OOK encoded), transmitted at a data rate of 1 Mb/sec (1 MHz), may be implemented with a transmit tag repetition rate of 1 transmission per second (1 TX/sec). Such an implementation may accommodate a battery life of up to seven years, wherein the battery itself may be, for example, a compact, 3-volt coin cell of the series no. BR2335 (Rayovac), with a battery charge rating of 300 mAhr. An alternate implementation may be a generic compact, 3-volt coin cell, series no. CR2032, with a battery charge rating of 220 mAhr, whereby the latter generic coin cell, as can be appreciated, may provide for a shorter battery life.

Alternatively or additionally, some applications may require higher transmit tag repetition rates to track a dynamic environment. In some examples, the transmit tag repetition rate may be 12 transmissions per second (12 TX/sec). In such applications, it can be further appreciated that the battery life may be shorter.

The high burst data transmission rate (e.g., 1 MHz), coupled with the short data packet length (e.g., 112 bits) and the relatively low repetition rates (e.g., 1 TX/sec), provide for two distinct advantages in some examples: (1) a greater number of tags may transmit independently from the field of tags with a lower collision probability, and/or (2) each independent tag transmit power may be increased, with proper consideration given to a battery life constraint, such that a total energy for a single data packet is less than a regulated average power for a given time interval (e.g., a 1 msec time interval for an FCC regulated transmission).

Alternatively or additionally, additional sensor or telemetry data may be transmitted from the tag to provide the receivers 106 with information about the environment and/or operating conditions of the tag. For example, the tag may transmit a temperature to the receivers 106. Such information may be valuable, for example, in a system involving perishable goods or other refrigerant requirements. In this example embodiment, the temperature may be transmitted by the tag at a lower repetition rate than that of the rest of the data packet. For example, the temperature may be transmitted from the tag to the receivers at a rate of one time per minute (e.g., 1 TX/min.), or in some examples, once every 720 times the data packet is transmitted, whereby the data packet in this example is transmitted at an example rate of 12 TX/sec.

Alternatively or additionally, the tag 102 may be programmed to intermittently transmit data to the receivers 106 in response to a signal from a magnetic command transmitter (not shown). The magnetic command transmitter may be a portable device, functioning to transmit a 125 kHz signal, in some example embodiments, with a range of approximately 15 feet or less, to one or more of the tags 102. In some examples, the tags 102 may be equipped with at least a receiver tuned to the magnetic command transmitter transmit frequency (e.g., 125 kHz) and functional antenna to facilitate reception and decoding of the signal transmitted by the magnetic command transmitter.

In some examples, one or more other tags, such as a reference tag 104, may be positioned within and/or about a monitored region. In some examples, the reference tag 104 may be configured to transmit a signal that is used to measure the relative phase (e.g., the count of free-running counters) of non-resettable counters within the receivers 106.

One or more (e.g., preferably four or more) receivers 106 are also positioned at predetermined coordinates within and/or around the monitored region. In some examples, the receivers 106 may be connected in a "daisy chain" fashion to advantageously allow for a large number of receivers 106 to be interconnected over a significant monitored region in order to reduce and simplify cabling, provide power, and/or the like. Each of the receivers 106 includes a receiver for receiving transmissions, such as UWB transmissions, and preferably, a packet decoding circuit that extracts a time of arrival (TOA) timing pulse train, transmitter ID, packet number, and/or other information that may have been encoded in the tag transmission signal (e.g., material description, personnel information, etc.) and is configured to sense signals transmitted by the tags 102 and one or more reference tags 104.

Each receiver 106 includes a time measuring circuit that measures times of arrival (TOA) of tag bursts, with respect to its internal counter. The time measuring circuit is phase-locked (e.g., phase differences do not change and therefore respective frequencies are identical) with a common digital reference clock signal distributed via cable connection from a Central Processor/Hub 108 having a central timing reference clock generator. The reference clock signal establishes a common timing reference for the receivers 106. Thus, multiple time measuring circuits of the respective receivers 106 are synchronized in frequency, but not necessarily in phase. While there typically may be a phase offset between any given pair of receivers in the receivers 106, the phase offset is readily determined through use of a reference tag 104. Alternatively or additionally, each receiver may be synchronized wirelessly via virtual synchronization without a dedicated physical timing channel.

In some example embodiments, the receivers 106 are configured to determine various attributes of the received signal. Since measurements are determined at each receiver 106, in a digital format, rather than analog in some examples, signals are transmittable to the Central Processor/Hub 108. Advantageously, because packet data and measurement results can be transferred at high speeds to a receiver memory, the receivers 106 can receive and process tag (and corresponding object) locating signals on a nearly continuous basis. As such, in some examples, the receiver memory allows for a high burst rate of tag events (i.e., information packets) to be captured.

Data cables or wireless transmissions may convey measurement data from the receivers 106 to the Central Processor/Hub 108 (e.g., the data cables may enable a transfer speed of 2 Mbps). In some examples, measurement data is transferred to the Central Processor/Hub at regular polling intervals.

As such, the Central Processor/Hub 108 determines or otherwise computes tag location (i.e., object position) by processing TOA measurements relative to multiple data packets detected by the receivers 106. In some example embodiments, the Central Processor/Hub 108 may be configured to resolve the coordinates of a tag using nonlinear optimization techniques.

In some examples, TOA measurements from multiple receivers 106 are processed by the Central Processor/Hub 108 to determine a position of the transmit tag 102 by a differential time-of-arrival (DTOA) analysis of the multiple TOAs. The DTOA analysis includes a determination of tag transmit time $t_0$, whereby a time-of-flight (TOF), measured as the time elapsed from the estimated tag transmit time $t_0$ to the respective TOA, represents graphically the radii of spheres centered at respective receivers 106. The distance between the surfaces of the respective spheres to the estimated position coordinates $(x_0, y_0, z_0)$ of the transmit tag 102 represents the measurement error for each respective TOA, and the minimization of the sum of the squares of the TOA measurement errors from each receiver participating in the DTOA position estimate provides for both the position coordinates $(x_0, y_0, z_0)$ of the transmit tag and of that tag's transmit time $t_0$.

In some examples, the system described herein may be referred to as an "over-specified" or "over-determined" system. As such, the Central Processor/Hub 108 may calculate one or more valid (i.e., most correct) positions based on a set of measurements and/or one or more incorrect (i.e., less correct) positions. For example, a position may be calculated that is impossible due the laws of physics or may be an outlier when compared to other calculated positions. As such one or more algorithms or heuristics may be applied to minimize such error.

The starting point for the minimization may be obtained by first doing an area search on a coarse grid of x, y and z over an area defined by the user and followed by a localized steepest descent search. The starting position for this algorithm is fixed, in some examples, at the mean position of all active receivers. No initial area search is needed, and optimization proceeds through the use of a Davidon-Fletcher-Powell (DFP) quasi-Newton algorithm in some examples. In other examples, a steepest descent algorithm may be used.

One such algorithm for error minimization, which may be referred to as a time error minimization algorithm, may be described in Equation 1:

$$\epsilon = \Sigma_{j=i}^{N} [[(x-x_j)^2 + (y-y_j)^2 + (z-z_j)^2]^{1/2} - c(t_j - t_0)]^2 \quad (1)$$

Where N is the number of receivers, c is the speed of light, $(x_j, y_j, z_j)$ are the coordinates of the $j^{th}$ receiver, $t_j$ is the arrival time at the $j^{th}$ receiver, and $t_0$ is the tag transmit time. The variable $t_0$ represents the time of transmission. Since $t_0$ is not initially known, the arrival times, $t_j$, as well as $t_0$, are related to a common time base, which in some examples, is derived from the arrival times. As a result, differences between the various arrival times have significance for determining location as well as $t_0$.

The optimization algorithm to minimize the error $\epsilon$ in Equation 1 may be the Davidon-Fletcher-Powell (DFP) quasi-Newton algorithm, for example. In some examples, the optimization algorithm to minimize the error $\epsilon$ in Equation 1 may be a steepest descent algorithm. In each case, the algorithms may be seeded with an initial position estimate (x, y, z) that represents the two-dimensional (2D) or three-dimensional (3D) mean of the positions of the receivers 106 that participate in the tag position determination.

In some examples, the RTLS system comprises a receiver grid, whereby each of the receivers 106 in the receiver grid keeps a receiver clock that is synchronized, with an initially unknown phase offset, to the other receiver clocks. The phase offset between any receivers may be determined by use of a reference tag that is positioned at a known coordinate position $(x_T, y_T, z_T)$. The phase offset serves to resolve the constant offset between counters within the various receivers 106, as described below.

In further example embodiments, a number N of receivers 106 $\{R_j: j=1, \ldots, N\}$ are positioned at known coordinates $(x_{R_j}, y_{R_j}, z_{R_j})$, which are respectively positioned at distances $d_{R_j}$ from a reference tag 104, such as given in Equation 2:

$$d_{R_j} = \sqrt{(x_{R_j} - X_T)^2 + (y_{R_j} - y_T)^2 + (z_{R_j} - z_T)^2} \quad (2)$$

Each receiver $R_j$ utilizes, for example, a synchronous clock signal derived from a common frequency time base, such as a clock generator. Because the receivers are not synchronously reset, an unknown, but constant offset $O_j$ exists for each receiver's internal free running counter. The value of the constant offset $O_j$ is measured in terms of the number of fine resolution count increments (e.g., a number of nanoseconds for a one nanosecond resolution system).

The reference tag is used, in some examples, to calibrate the radio frequency locating system as follows: The reference tag emits a signal burst at an unknown time $\tau_R$. Upon receiving the signal burst from the reference tag, a count $N_{R_j}$ as measured at receiver $R_j$ is given in Equation 3 by:

$$N_{R_j} = \beta \tau_R + O_j + \beta d_{R_j}/c \quad (3)$$

Where c is the speed of light and $\beta$ is the number of fine resolution count increments per unit time (e.g., one per nanosecond). Similarly, each object tag $T_i$ of each object to be located transmits a signal at an unknown time $\tau_i$ to produce a count $N_{ij}$, as given in Equation 4:

$$N_{ij} = \beta \Sigma_i + O_j + \beta d_{ij}/c \quad (4)$$

at receiver $R_j$ where $d_{ij}$ the distance between the object tag $T_i$ and the receiver 106 $R_j$. Note that $\tau_i$ is unknown, but has the same constant value for all receivers. Based on the equalities expressed above for receivers $R_j$ and $R_k$ and given the reference tag 104 information, phase offsets expressed as differential count values are determined as given in Equations 5a-b:

$$N_{R_j} - N_{R_k} = (O_j - O_k) + \beta \left( \frac{d_{R_j}}{c} - \frac{d_{R_k}}{c} \right) \quad (5a)$$

Or, $$(O_j - O_k) = (N_{R_j} - N_{R_k}) - \beta\left(\frac{d_{R_j}}{c} - \frac{d_{R_k}}{c}\right) = \Delta_{jk} \quad (5b)$$

Where $\Delta_{jk}$ is constant as long as $d_{R_j} - d_{R_k}$ remains constant, (which means the receivers and reference tag are fixed and there is no multipath situation) and $\beta$ is the same for each receiver. Note that $\Delta_{jk}$ is a known quantity, since $N_{R_j}$, $N_{R_k}$, $\beta$, $d_{R_j}/c$, and $d_{R_k}/c$ are known. That is, the phase offsets between receivers $R_j$ and $R_k$ may be readily determined based on the reference tag 104 transmissions. Thus, again from the above equations, for a tag 102 ($T_i$) transmission arriving at receivers $R_j$ and $R_k$, one may deduce the following Equations 6a-b:

$$N_{i_j} - N_{i_k} = (O_j - O_k) + \beta\left(\frac{d_{i_j}}{c} - \frac{d_{i_k}}{c}\right) = \Delta_{jk} + \beta\left(\frac{d_{i_j}}{c} - \frac{d_{i_k}}{c}\right) \quad (6a)$$

Or, $$d_{i_j} - d_{i_k} = (c/\beta)[N_{i_j} - N_{i_k} - \Delta_{jk}] \quad (6b)$$

Each arrival time, $t_j$, can be referenced to a particular receiver (receiver "1") as given in Equation 7:

$$t_j = \frac{1}{\beta}(N_j - \Delta_{j1}) \quad (7)$$

The minimization, described in Equation 1, may then be performed over variables (x, y, z, $t_0$) to reach a solution (x', y', z', $t_0'$).

In some example embodiments, the location of a tag 102 may then be output to the receiver processing and distribution system 110 for further processing of the location data to advantageously provide visualizations, predictive analytics and/or the like.

The exemplary radio frequency locating system of FIG. 1 may be used in providing the location of a tag to be associated with a participant in accordance with some embodiments of the present invention. In the environment of FIG. 1, data may be captured and analyzed, such as during a sporting event to identify participants, events, statistics, and other data useful to a sports team, league, viewer, licensee, or the like. In some embodiments, data associated with a number of objects or participants (e.g., players, officials, balls, game equipment, etc.) on a playing field, such as monitored region 100, may be generated and provided to a performance analytics system. As such, as further discussed in connection with FIGS. 2a-c below, each object may have one or more attached tags 102 (such as to equipment worn by a player) to be used to track data such as location, change of location, speed, or the like of each object. In some embodiments, additional sensors, such as accelerometers, health sensors, temperature sensors, moisture sensors, light sensors, or the like, may be attached to each object to provide further data to the performance analytics system. Such additional sensors may provide data to the tag 102, either through a wired or wireless connection, to be transmitted to the receivers 106 or the sensors may be configured to transmit data to dedicated receivers separately from tags 102.

One or more of the receivers 106 may receive transmissions from tags 102 and transmit the tag data to a receiver hub 108. The receiver hub 108 may process the received data to determine a tag location for the tags 102. The receiver hub 108 may transmit the tag location data to one or more processors, such as receiver processing and distribution system 110. Receiver processing and distribution system 110 may use one or more modules (e.g., processing engines) and one or more databases to identify the object each of the tags 102 is associated with, such as a player, official, ball, or the like.

In some embodiments, multiple tags 102 (as well as other sensors) may be attached to the equipment worn by a participant (e.g., an individual player or official). The receiver processing and distribution system 110 may use a database to associate the tag identifier of each tag 102 with each player, official, object, or other participant and correlate the tag location data and/or other sensor data for multiple tags 102 that are associated with a particular player, official, object, or other participant. As discussed in greater detail below, the receiver processing and distribution system 110 may then use the tag location data to determine player dynamics, such as a player's location, how the location is changing with time, velocity, acceleration, deceleration, total yardage, or the like. The receiver processing and distribution system 110 may also use the tag location data and sensor derived data to determine the identity of a participant for association of the tag with the particular participant. The receiver processing and distribution system 110 may also use the data and one or more databases to determine team formations, play activity, events, statistics, or the like, such as by comparing the data to various models to determine the most likely formation or play or the events that have occurred during a game. The receiver processing and distribution system 110 may also use the data to provide statistics or other output data for the players, teams, and the game.

Example Tag/Sensor Positioning and Participant Correlation

FIG. 1 shows a monitored area 100. The monitored area 100 comprises a plurality of positions at one or more time epochs. The plurality of positions may be divided into one or more regions, called zones. Each zone may be described by one or more coordinate systems, such as a local NED (North-East-Down) system, a latitude-longitude system, or even a yard line system as might be used for an American football game. A location is a description of a position, or a plurality of positions, within the monitored area. For example, a field marker at the intersection of the south goal line and west out of bounds line at Bank of America Stadium in Charlotte, N.C. could be described as {0,0,0} in a local NED system, or 35.225336 N 80.85273 W longitude 751 ft. altitude on a latitude-longitude system, or simply "Panthers Goal Line" in a yard line system. Because different types of locating systems or different zones within a single locating system may use different coordinate systems, a Geographical Information System or similar monitored area database may be used to associate location data. One type of Geographical Information System describing at least a field of play may be called Field Data.

FIGS. 2A-C illustrate some exemplary participants that may provide information to a performance analytics system in accordance with some embodiments of the present invention. FIG. 2A illustrates a player 202 (e.g., a football player) wearing equipment having attached tags 102 in accordance with some embodiments. In particular, the depicted player 202 is wearing shoulder pads having tags 102 affixed to opposite sides thereof. This positioning advantageously provides an elevated broadcast position for each tag 102 thereby increasing its communication effectiveness.

Additional sensors 203 may be attached to equipment worn by player 202, such as accelerometers, magnetometers, time-of-flight sensors, health monitoring sensors (e.g., blood pressure sensors, heart monitors, respiration sensors, moisture sensors, temperature sensors), light sensors, or the like. The additional sensors 203 may be affixed to shoulder pads, the helmet, the shoes, rib pads, elbow pads, the jersey, the pants, a bodysuit undergarment, gloves, arm bands, wristbands, and the like.

Sensors 203 may be configured to communicate with receivers (e.g., receivers 106 of FIG. 1) directly or indirectly through tags 102 or other transmitters. For example, in one embodiment, a sensor 203 may be connected, wired (e.g., perhaps through wires sewn into a jersey or bodysuit undergarment) or wirelessly, to tags 102 to provide sensor derived data to tags 102, which is then transmitted to the receivers 106. In another embodiment, a plurality of sensors (not shown) may be connected to a dedicated antenna or transmitter, perhaps positioned in the helmet, which may transmit sensor derived data to one or more receivers.

FIG. 2B illustrates a game official 206 wearing equipment having attached tags 102 and sensors 203 in accordance with some embodiments. In the depicted embodiment, tags 102 are attached to the official's jersey proximate opposite shoulders. Sensors 203 are positioned in wristbands worn on the official's wrists as shown. Sensors 203 may be configured to communicate with receivers (e.g., receivers 106 of FIG. 1) directly or indirectly through tags 102 or other transmitters as discussed above in connection with FIG. 2A.

As discussed in greater detail below, the positioning of sensors 203 (here, accelerometers) proximate the wrists of the official may allow the receiver processing and distribution system 110 to determine particular motions, movements, or activities of the official 206 for use in determining events (e.g., winding of the game clock, first down, touchdown, or the like). The official 206 may also carry other equipment, such as penalty flag 208, which may also have a tag 102 (and optionally one or more sensors) attached to provide additional data to the receiver processing and distribution system 110. For example, the receiver processing and distribution system 110 may use tag location data from the penalty flag 208 to determine when the official is merely carrying the penalty flag 208 versus when the official is using the penalty flag 208 to indicate an event, such as a penalty (e.g., by throwing the penalty flag 208).

FIG. 2C illustrates an example of a ball 210 having tags 102 attached or embedded in accordance with some embodiments. Additionally, sensors 203 may be attached to or embedded in the ball 210, such as accelerometers, time-of-flight sensors, or the like. In some embodiments, the sensor 203 may be connected, wired or wirelessly, to tag 102 to provide sensor data to tag 102 which is then transmitted to the receivers 106. In some embodiments, the sensor 203 may transmit sensor data to receivers separately from the tag 102, such as described above in connection with FIG. 2A.

As will be apparent to one of ordinary skill in the art in view of this disclosure, once the tags 102 and sensors 203 of FIGS. 2A-C are positioned on participants, they may be correlated to such participants. For example, in some embodiments, unique tag or sensor identifiers ("unique IDs") may be correlated to a participant profile (e.g., John Smith—running back, Fred Johnson—line judge official, or ID 027—one of several game balls, etc.) and stored to a remote database accessible to the performance analytics system as discussed in greater detail below. Each participant profile may further include or be correlated with a variety of data including, but not limited to, biometric data (e.g., height, weight, health data, etc.), role data, team ID, performance statistics, and other data that may be apparent to one of skill in the art in view of the foregoing description.

In some embodiments, such participant profile or role data may be pre-defined and stored in association with the unique tag or sensor identifiers. In other embodiments, the participant profile or role data may also be "learned" by the system as a result of received tag or sensor data, formation data, play data, event data, and/or the like. For example, in some embodiments the system may determine that a tag or sensor is not correlated to a participant profile and may analyze data received from the tag and/or sensor to determine possible participant roles, etc., which may be ranked and then selected/confirmed by the system or by a user after being displayed by the system. In some embodiments, the system may determine possible participant roles (i.e., participant role data) based on determined participant location data (e.g., movement patterns, alignment position, etc.).

In some embodiments, as described in greater detail below, the participant profile or role data may also be updated by the system (i.e., to produce a data set for the participant that is far more robust than that established at initial registration) as a result of received tag or sensor data, formation data, play data, event data, and/or the like. In some embodiments, the participant profile and/or role data may be used in a performance analytics system to weight the actions of the participants during analysis to assist in qualifying what is occurring, such as in determining formations, plays, events, etc.

Tag ID and Sensor Data Transmission Architecture

FIGS. 3A, 3B, 3C, 3D, and 3E show block diagrams of various different architectures that may be utilized in transmitting signals from one or more tags and sensors to one or more receivers of a receiver processing and analytics system in accordance with embodiments of the invention. In some embodiments, the depicted architectures may be used in connection with the receiver processing and analytics system 110 of FIG. 1. More than one of these architectures may be used together in a single system.

FIG. 3A shows a RF location tag 102, such as that shown in FIG. 1, which may be configured to transmit a tag signal to one or more receivers 106. The one or more receivers 106 may transmit a receiver signal to the receiver hub/locate engine 108.

The depicted RF location tag 102 may generate or store a tag unique identifier ("tag UID") and/or tag data as shown. The tag data may include useful information such as the installed firmware version, last tag maintenance date, configuration information, and/or a tag-participant correlator. The tag-participant correlator may comprise data that indicates that a monitored participant is associated with the RF location tag 102 (e.g., name, uniform number and team, biometric data, tag position on the participant, i.e., right wrist). As will be apparent to one of skill in the art in view of this disclosure, the tag-participant correlator may be stored to the RF location tag 102 when the tag is registered or otherwise associated with a participant. While shown as a separate field for illustration purposes, one of ordinary skill in the art may readily appreciate that the tag-participant correlator may be part of any tag data or even omitted from the tag.

The tag signal transmitted from RF location tag 102 to receiver 106 may include "blink data" as it is transmitted at selected intervals. This "blink rate" may be set by the tag designer or the system designer to meet application requirements. In some embodiments it is consistent for one or all tags; in some embodiments it may be data dependent. Blink data includes characteristics of the tag signal that allow the tag signal to be recognized by the receiver 106 so the location of the RF location tag 102 may be determined by the locating system. Blink data may also comprise one or more tag data packets. Such tag data packets may include any data from the tag 102 that is intended for transmission such as, for example in the depicted embodiment, a tag UID, tag data, and a tag-participant correlator. In the case of TDOA systems, the blink data may be or include a specific pattern, code, or trigger that the receiver 106 (or downstream receiver processing and analytics system) detects to identify that the transmission is from a RF location tag 102 (e.g., a UWB tag).

The depicted receiver 106 receives the tag signal, which includes blink data and tag data packets as discussed above. In one embodiment, the receiver 106 may pass the received tag signal directly to the receive hub/locate engine 108 as part of its receiver signal. In another embodiment, the receiver 106 could perform some basic processing on the received tag signal. For instance, the receiver could extract blink data from the tag signal and transmit the blink data to the receive hub/locate engine 108. The receiver could transmit a time measurement to the receive hub/locate engine 108 such as a TOA measurement and/or a TDOA measurement. The time measurement could be based on a clock time generated or calculated in the receiver, it could be based on a receiver offset value as explained above, it could be based on a system time, and/or it could be based on the time difference of arrival between the tag signal of the RF location tag 102 and the tag signal of a RF reference tag (e.g., tag 104 of FIG. 1). The receiver 106 could additionally or alternatively determine a signal measurement from the tag signal (such as a received signal strength indication (RSSI), a direction of signal, signal polarity, or signal phase) and transmit the signal measurement to the receive hub/locate engine 108.

FIG. 3B shows a RF location tag 202 and sensor 203, such as those associated with a participant as shown in FIG. 2, which may be configured to transmit tag signals and sensor signals, respectively, to one or more receivers 106, 166. The one or more receivers 106, 166 may then transmit receiver signals to the receiver hub/locate engine 108. One or more receivers 106, 166 may share physical components, such as a housing or antenna.

The depicted RF location tag 202 may comprise a tag UID and tag data (such as a tag-participant correlator) and transmit a tag signal comprising blink data as discussed in connection with FIG. 3A above. The depicted sensor 203 may generate and/or store a sensor UID, additional stored sensor data (e.g. a sensor-participant correlator, sensor type, sensor firmware version, last maintenance date, the units in which environmental measurements are transmitted, etc.), and environmental measurements. The "additional stored sensor data" of the sensor 203 may include any data that is intended for transmission, including but not limited to a RF location tag 202, a reference tag (e.g., 104 of FIG. 1), a sensor receiver, a receiver 106, and/or the receiver/hub locate engine 108.

The sensor-participant correlator may comprise data that indicates that a monitored participant is associated with the sensor 203 (e.g., name, uniform number and team, biometric data, sensor position on participant, i.e., right wrist). As will be apparent to one of skill in the art in view of this disclosure, the sensor-participant correlator may be stored to the sensor 203 when the sensor is registered or otherwise associated with a participant. While shown as a separate field for illustration purposes, one of ordinary skill in the art may readily appreciate that the sensor-participant correlator may be part of any additional stored sensor data or omitted from the sensor altogether.

Sensors such as sensor 203 that are structured according to embodiments of the invention may sense or determine one or more environmental conditions (e.g. temperature, pressure, pulse, heartbeat, rotation, velocity, acceleration, radiation, position, chemical concentration, voltage) and store or transmit "environmental measurements" that are indicative of such conditions. To clarify, the term "environmental measurements" includes measurements concerning the environment proximate the sensor including, without limitation, ambient information (e.g., temperature, position, humidity, etc.) and information concerning a participant's health, fitness, operation, and/or performance. Environmental measurements may be stored or transmitted in either analog or digital form and may be transmitted as participant measurements, as a set of participant measurements, and/or as summary statistics. For example, temperature in degrees Celsius may be transmitted as {31}, or as {33, 32, 27, 22, 20, 23, 27, 30, 34, 31}, or as {27.9}. In some embodiments, the sensor-participant correlator could be determined at least in part from the environmental measurements.

In the depicted embodiment, RF location tag 202 transmits a tag signal to receiver 106 and sensor 203 transmits a sensor signal to sensor receiver 166. The sensor signal may comprise one or more sensor information packets. Such sensor information packets may include any data or information from the sensor 203 that is intended for transmission such as, for example in the depicted embodiment, sensor UID, additional stored sensor data, sensor-participant correlator, and environmental measurements. A receiver signal from receiver 106 and a sensor receiver signal from sensor receiver 166 may be transmitted via wired or wireless communication to receiver hub/locate engine 108 as shown.

FIG. 3C depicts a sensor 203 communicating through a RF location tag 202 in accordance with various embodiments. In one embodiment, the sensor 203 may be part of (i.e., reside in the same housing or assembly structure) of the RF location tag 202. In another embodiment, the sensor 203 may be distinct from (i.e., not resident in the same housing or assembly structure) the RF location tag 202 but configured to communicate wirelessly or via wired communication with the RF location tag 202.

In one embodiment, the RF location tag 202, the sensor 203, or both, may generate and/or store a tag-sensor correlator that indicates an association between a RF location tag 202 and a sensor 203 (e.g., tag UID/sensor UID, distance from tag to sensor in a particular stance, set of sensors associated with a set of tags, sensor types associated with a tag, etc.). In the depicted embodiment, both the RF location tag 202 and the sensor 203 store the tag-sensor correlator.

In the depicted embodiment, sensor 203 transmits a sensor signal to RF location tag 202. The sensor signal may comprise one or more sensor information packets as discussed above. The sensor information packets may comprise the sensor UID, a sensor-participant correlator, additional stored sensor data, the tag-sensor correlator, and/or the environmental measurements. The RF location tag 202 may store some portion of, or all of, the sensor information packets locally and may package the sensor information packets into one or more tag data packets for transmission to receiver 106 as part of a tag signal or simply pass them along as part of its tag signal.

FIG. 3D illustrates an example communication structure for a reference tag 104 (e.g., reference tag 104 of FIG. 1), an RF location tag 202, a sensor 203, and two receivers 106 in accordance with one embodiment. The depicted reference tag 104 is a RF location tag and thus may include tag data, a tag UID, and is capable of transmitting tag data packets. In some embodiments, the reference tag 104 may form part of a sensor and may thus be capable of transmitting sensor information packets.

The depicted sensor 203 transmits a sensor signal to RF reference tag 104. The RF reference tag 104 may store some portion or some or all of the sensor information packets locally and may package the sensor information packets into one or more tag data packets for transmission to receiver 106 as part of a tag signal, or simply pass them along as part of its tag signal.

As was described above in connection with FIG. 1, the receivers 106 of FIG. 3D are configured to receive tag signals from the RF location tag 202 and the reference tag 104. Each of these tag signals may include blink data, which may comprise tag UIDs, tag data packets, and/or sensor information packets. The receivers 106 each transmit receiver signals via wired or wireless communication to the receiver hub/locate engine 108 as shown.

FIG. 3E illustrates an example communication structure between an RF location tag 202, a plurality of receivers 106, and a variety of sensor types including, without limitation, a sensor 203, a diagnostic device 233, a triangulation positioner 243, a proximity positioner 253, and a proximity label 263 in accordance with various embodiments. In the depicted embodiment, none of the sensors 203, 233, 243, 253 form part of an RF location tag 202 or reference tag 104. However, each may comprise a sensor UID and additional stored sensor data. Each of the depicted sensors 203, 233, 243, 253 transmits sensor signals comprising sensor information packets.

In the depicted embodiment, receiver 106 is configured to receive a tag signal from RF location tag 202 and a sensor signal directly from sensor 203. In such embodiments, sensor 203 may be configured to communicate in a communication protocol that is common to RF location tag 202 as will be apparent to one of ordinary skill in the art in view of this disclosure.

FIG. 3E depicts one type of sensor referred to herein as a "proximity interrogator". The proximity interrogator 223 can include circuitry operative to generate a magnetic, electromagnetic, or other field that is detectable by a RF location tag 202. While not shown in FIG. 3E, a proximity interrogator 223 may include a sensor UID and other tag and sensor derived data or information as discussed above.

In some embodiments, the proximity interrogator 223 is operative as a proximity communication device that can trigger a RF location tag 202 (e.g., when the RF location tag 202 detects the field produced by the proximity interrogator 223) to transmit blink data under an alternate blink pattern or blink rate. The RF location tag can initiate a preprogrammed (and typically faster) blink rate to allow more location points for tracking a participant. In some embodiments, the RF location tag may not transmit a tag signal until triggered by the proximity interrogator 223. In some embodiments the RF location tag 202 may be triggered when the RF location tag 202 moves near (e.g., within communication proximity to) a proximity interrogator 223.

In some embodiments, the RF location tag may be triggered when the proximity interrogator 223 moves near to the RF location tag 202.

In other embodiments, the RF location tag 202 may be triggered when a button is pressed or a switch is activated on the proximity interrogator 223 or on the RF location tag itself. For example, a proximity interrogator 223 could be placed at the start line of a racetrack. Every time a car passes the start line, a car-mounted RF location tag 202 senses the signal from the proximity interrogator and is triggered to transmit a tag signal indicating that a lap has been completed. As another example, a proximity interrogator 223 could be placed at a Gatorade cooler. Each time a player or other participant fills a cup from the cooler a participant-mounted RF location tag 202 senses the signal from the proximity interrogator and is triggered to transmit a tag signal indicating that Gatorade has been consumed. As another example, a proximity interrogator 223 could be placed on a medical cart. When paramedics use the medical cart to pick up a participant (e.g., a player) and move him/her to the locker room, a participant-mounted RF location tag 202 senses the signal from the proximity interrogator and is triggered to transmit a tag signal indicating that they have been removed from the game. As explained, any of these post-triggered tag signals may differ from pre-triggered tag signals in terms of any aspect of the analog and/or digital attributes of the transmitted tag signal.

FIG. 3E depicts another type of sensor that is generally not worn by a participant but is referred to herein as a "diagnostic device". However, like other sensors, diagnostic devices may measure one or more environmental conditions and store corresponding environmental measurements in analog or digital form.

While the depicted diagnostic device 233 is not worn by a participant, it may generate and store a sensor-participant correlator for association with environmental measurements taken in connection with a specific participant. For example, in one embodiment, the diagnostic device 233 may be a blood pressure meter that is configured to store as environmental measurements blood pressure data for various participants. Each set of environmental measurements (e.g., blood pressure data) may be stored and associated with a sensor-participant correlator.

The depicted diagnostic device 233 is configured to transmit a sensor signal comprising sensor information packets to a sensor receiver 166. The sensor information packets may comprise one or more of the sensor UID, the additional stored data, the environmental measurements, and/or the sensor-participant correlator as discussed above. The sensor receiver 166 may associate some or all of the data from the sensor information packets with other stored data in the sensor receiver 166 or with data stored or received from other sensors, diagnostic devices, RF location tags 102, or reference tags. The sensor receiver 166 transmits a sensor receiver signal to a receiver hub/locate engine 108.

Another type of sensor shown in FIG. 3E is a triangulation positioner 243. A "triangulation positioner" is a type of sensor that senses position. The depicted triangulation positioner 243 includes a sensor UID, additional stored sensor data, and environmental measurements as discussed above.

In some embodiments, a triangulation positioner (also known as a global positioning system (GPS) receiver) receives clock data transmitted by one or more geostationary satellites (a satellite in a known or knowable position) and/or one or more ground based transmitters (also in known or knowable positions), compares the received clock data, and computes a "position calculation". The position calculation may be included in one or more sensor information packets as environmental measurements.

In another embodiment, a triangulation positioner comprises one or more cameras or image-analyzers that receive emitted or reflected light or heat, and then analyzes the received images to determine the location of a participant or sensor. Although a triangulation positioner may transmit data wirelessly, it is not a RF location tag because it does not transmit blink data or a tag signal that can be used by a receiver hub/locate engine 108 to calculate location. In contrast, a triangulation positioner senses position and computes a position calculation that may then be used as environmental measurements by the receiver hub/locate engine 108.

In one embodiment, a triangulation positioner could be combined with a RF location tag or reference tag (not shown). In such embodiments, the triangulation positioner could compute and transmit its position calculation via the RF location tag to one or more receivers. However, the receiver hub/locate engine would calculate tag location based on the blink data received as part of the tag signal and not based solely on the position calculation. The position calculation would be considered as environmental measurements and may be included in associated sensor information packets.

As will be apparent to one of ordinary skill in the art, position calculations (e.g., GPS receiver position calculations) are not as accurate as the location calculations (e.g., UWB waveform based location calculations) performed by receiver hub/locate engines structured in accordance with various embodiments of the invention. That is not to say that position calculations may not be improved using known techniques. For example, a number of influences, including atmospheric conditions, can cause GPS accuracy to vary over time. One way to control this is to use a differential global positioning system (DGPS) comprising one or a network of stationary triangulation positioners that are placed in a known position, and the coordinates of the known position are stored in memory as additional stored sensor data. These triangulation positioners receive clock data from geostationary satellites, determine a position calculation, and broadcast a difference between the position calculation and the stored coordinates. This DGPS correction signal can be used to correct for these influences and significantly reduce location estimate error.

Another type of sensor shown in FIG. 3E is a proximity detector 253. A "proximity detector" is a type of sensor that senses identity within an area (e.g., a local area) that is small with respect to the monitored area 100 of FIG. 1. Many different ways of sensing identity (e.g., a unique ID or other identifier for a sensed object or participant) would be apparent to one of ordinary skill in the art in view of this disclosure including, without limitation, reading a linear bar code, reading a two-dimensional bar code, reading a near field communication (NFC) tag, reading a RFID tag such as a UHF tag, HF tag, or low frequency tag, an optical character recognition device, a biometric scanner, or a facial recognition system.

In some embodiments, a proximity detector senses an attribute of a participant (or a participant's wristband, tag, label, card, badge, clothing, uniform, costume, phone, ticket, etc.). The identity sensed by a proximity detector may be stored locally at the proximity detector 253 as shown and transmitted as environmental measurements via one or more sensor information packets to a sensor receiver 166.

In some embodiments, a proximity detector 253 may have a defined position, which is often stationary, and may be associated with a location in the monitored area 100 of FIG. 1. For example, a proximity detector 253 could be located at a finish line of a race track, an entrance gate of a stadium, with a diagnostic device, at a goal line or goal post of a football field, at a base or home plate of a baseball diamond, or a similar fixed location. In such embodiments where the proximity detector is stationary, the position coordinates of the proximity detector and a sensor UID could be stored to a monitored area database (not shown) that is accessible by one or more of the receivers 106, 166, the receiver hub/locate engine 108, and/or other components of the receiver processing and analytics system 110. In embodiments where the proximity detector is movable, a position calculation could be determined with a triangulation positioner, or the proximity detector could be combined with a RF location tag and located by the receiver hub/locate engine 108. While shown as separate fields for illustration purposes in FIG. 3E, identify information and position calculation could comprise part of the additional stored sensor data, the environmental measurements, or both.

In one embodiment, the proximity detector could be associated with a reference tag (e.g., tag 104 of FIG. 1) whose position is recorded in the monitored area database. In other embodiments, the proximity detector is movable, such that it may be transported to where it is needed. For example, a proximity detector 253 could be located on a medical cart, first down marker, a diagnostic device, goal post, or carried by a paramedic or security guard. In an embodiment where the proximity detector 253 is movable it would typically be associated with a RF location tag or triangulation positioner so that location (for a RF location tag) or position (for a triangulation positioner) can be determined at the time identity is sensed.

In the embodiment where the proximity detector includes a RF location tag, the receiver hub/locate engine 108 would locate the associated RF location tag, and the tag data/sensor data filter 112 would associate the tag location data for the associated RF location tag as the position of the proximity detector, while determining the identity of an associated participant from any received sensor information packets. In the alternate embodiment where the proximity detector includes a triangulation positioner, the triangulation positioner would compute a position calculation that could be stored as additional stored sensor data and/or environmental measurements, and transmitted as one or more sensor information packets. In one embodiment, sensor information packets for a proximity detector may include both sensed identity information and a position calculation.

Another type of sensor shown in FIG. 3E is a proximity label 263. A proximity label has a fixed position and an identification code (e.g., a sensor UID). The proximity label 263 may further comprise additional stored sensor data as shown. The depicted proximity label 263 is configured to be read by proximity detector 253. In some embodiments, proximity detector 253 may be further configured to write information to proximity label 263.

A proximity label 263 may be a sticker, card, tag, passive RFID tag, active RFID tag, NFC tag, ticket, metal plate, electronic display, electronic paper, inked surface, sundial, or otherwise visible or machine readable identification device as is known in the art. The coordinates of the position of the proximity label 263 are stored such that they are accessible to the receive hub/locate engine 108. For example, in one embodiment, the position coordinates of a proximity label 263 could be stored in a field database or monitored area database accessible via a network, or stored locally as additional stored data in the proximity detector 253.

In some embodiments, a position of the proximity label 263 is encoded into the proximity label 263 itself. For example, coordinates of a position of the proximity label 263 could be encoded into a passive RFID tag that is placed in that position. As another example, the coordinates of a position of the proximity label 263 could be encoded into a printed barcode that is placed in that position. As another example, a proximity label 263 comprising a NFC tag could be encoded with the location "end zone", and the NFC tag could be placed at or near an end zone at Bank of America stadium. In some embodiments, the stored coordinates of the proximity label 263 may be offset from the actual coordinates of the proximity label 263 by a known or determinable amount.

In one embodiment, a proximity label 263 such as an NFC tag may be encoded with a position. When a sensor such as a proximity detector approaches the NFC tag it may read the position, then transmit the position in a sensor information packet to the sensor receiver 166' and eventually to the receiver hub/locate engine 108. In another embodiment, a proximity label 263 such as a barcode label may be encoded with an identification code. When a smartphone with a proximity detector (such as a barcode imager) and a triangulation positioner (such as a GPS chip, GPS application, or similar device) approaches the barcode label it may read the identification code from the barcode, determine a position calculation from received clock data, then transmit the identity and the position calculation to sensor receiver 166' and eventually to the receiver hub/locate engine 106 as part of one or more sensor information packets.

In the depicted embodiment, triangulation positioner 243 and proximity detector 253 are each configured to transmit sensor signals carrying sensor information packets to sensor receiver 166'. The depicted sensors 243, 253, like any sensor discussed herein, may transmit sensor signals via wired or wireless communication protocols. For example, any proprietary or standard wireless protocol (e.g., 802.11, Zigbee, ISO/IEC 802.15.4, ISO/IEC 18000, IrDA, Bluetooth, CDMA, or any other protocol) could be used for the sensor signals. Alternatively or additionally, any standard or proprietary wired communication protocol (e.g., Ethernet, Parallel, Serial, RS-232, RS-422, USB, Firewire, I2C, etc.) may be used. Similarly, sensor receiver 166', and any receiver discussed herein, may use similar wired and wireless protocols to transmit receiver signals to the receiver hub/locate engine.

In one embodiment, upon receiving sensor signals from the triangulation positioner 243 and the proximity detector 253, the sensor receiver 166' may associate some or all of the data from the received sensor information packets with other data stored to the sensor receiver 166', or with data stored or received from other sensors (e.g., sensor 203), diagnostic devices 233, RF location tags 102, or RF reference tags 104. Such associated data is referred to herein as "associated sensor data". In the depicted embodiment, the sensor receiver 166' is configured to transmit some or all of the received sensor information packets and any associated sensor data to the receiver hub/locate engine 108 at part of a sensor receiver signal.

In one embodiment, a smartphone comprising a proximity detector (such as a barcode imager) and a triangulation positioner (such as a GPS chip) may associate an identification code determined from a barcode with a position calculation from received clock data as associated sensor data and transmit a sensor information packet that includes such associated sensor data to the receiver hub/locate engine 108. In another embodiment, the smartphone could transmit a first sensor information packet including the identification code and the smartphone's unique identifier to another sensor receiver, the smartphone could transmit a second sensor information packet including the position calculation and the smartphone's unique identifier to the sensor receiver, and the sensor receiver could associate the position calculation with the identification code based on the common smartphone unique identifier and transmit such associated sensor data to the receiver hub/locate engine 108. In another embodiment, the sensor receiver could determine a first time measurement associated with the first sensor information packet and a second time measurement associated with the second sensor information packet that, in conjunction with the sensor UID, could be used, by the receiver hub/locate engine 108, to associate the first sensor information packet with the second sensor information packet.

In one embodiment, the receiver hub/locate engine 108 receives receiver signals from the receiver 106 and sensor receiver signals from the sensor receivers 166, 166'. In the depicted embodiment, receiver 106 may receive blink data from the RF location tag 102 and transmits to the receiver hub/locate engine 108 some or all of the blink data, perhaps with additional time measurements or signal measurements. In some embodiments, time measurements or signal measurements may be based on a tag signal received from a RF reference tag (e.g., reference tag 104 of FIG. 1). The receiver hub/locate engine 108 collects the blink data, time measurements (e.g. time of arrival, time difference of arrival, phase), and/or signal measurements (e.g. signal strength, signal direction, signal polarization, signal phase) from the receivers 106 and computes tag location data for the tags 102 as discussed above in connection with FIG. 1. In some embodiments, the receivers 106 may be configured with appropriate RF filters, such as to filter out potentially interfering signals or reflections proximate the field of play or other area to be monitored.

The receiver hub/locate engine 108 may also access stored data or clock data from local storage and from a network location. The receiver hub/locate engine 108 uses this information to determine tag location data for each RF location tag. It may also associate data derived or extracted from tag signals transmitted from one or more RF location tags with information or data derived or extracted from sensor signals transmitted from one or more sensors.

In addition to the TOA or TDOA systems previously described, other real-time location systems (RTLS) such as received signal strength indication based systems could potentially be implemented by a receiver hub/locate engine 108. Any RTLS system using RF location tags, including those described herein, could require considerable processing by the receiver hub/locate engine 108 to determine the tag location data from the blink data received from the tags. These may require time measurement and/or signal measurement in addition to blink data, which preferably includes a tag UID. In contrast, in other systems, such as global position systems (GPS) systems, location data is determined based upon the position calculation transmitted from a GPS transmitter (also referred to as a GPS receiver or GPS tag) which includes calculated information about the location where the tag was positioned (i.e., coordinates determined at the tag via satellite signal triangulation, etc.) when the position calculation was determined or stored. Thus, GPS information typically refers to additional information that is transmitted along with a GPS transmitter ID before the transmission is received by a sensor receiver.

A GPS host device or back-end server may receive the GPS information and simply parse the position calculation (as opposed to calculating the position information at the host device) and the GPS transmitter ID into a data record. This data record may be used as a GPS position calculation, or it could be converted to a different coordinate system to be used as a GPS position calculation, or it could be processed further with DGPS information to be used as a GPS position calculation.

Returning to FIG. 3C, the depicted RF location tag 202 is used to convey (sometimes called backhaul) sensor information packets to a receiver 106. In some embodiments, while not shown, multiple sensors 203 may transmit sensor signals carrying sensor information packets to RF location tag 202. Such received sensor information packets may be associated with blink data that is transmitted to receiver 106.

In one embodiment, the receiver hub/locate engine 108 may parse sensor information packets from received tag data packets and associate such sensor information packets with the RF location tag 202 that transmitted the sensor information packet. Thus, the receiver hub/locate engine 108 may be able to determine tag location data, which may comprise a location and other data (e.g., tag data, tag UID, tag-participant correlator, sensor-participant correlator, additional stored sensor data, environmental measurements, tag-sensor correlator, identity information, position calculation, etc.) from one or more tags or sensors. Such data and information may be transmitted to the receiver processing and analytics system 110.

In some embodiments, once the receiver hub/locate engine 108 determines a location estimate of a RF location tag 102 at the time epoch of the tag signal, the receiver hub/locate engine 108 can also associate a location estimate with the tag data packet included in the blink data of such tag signal. In some embodiments, the location estimate of the tag signal may be used as tag location data for the tag data packet. In some embodiments a Geographical Information System (GIS) may be used by the receive hub/locate engine 108 to refine a location estimate, or to map a location estimate in one coordinate system to a location estimate in a different coordinate system, to provide a location estimate for the tag data packet.

In one embodiment, the location estimated for the tag data packet may be associated with any data in the tag data packet, including a tag UID, other tag data, and, if included, one or more sensor information packets, including sensor UID, additional stored sensor data, and environmental measurements. Since environmental measurements may include a position calculation from a triangulation positioner (e.g., a GPS device), the receiver hub/locate engine 108 could parse the position calculation and use it to refine a location estimate for the tag data packet.

Preferably, the receiver hub/locate engine 108 may access a participant database to determine tag-participant correlators or sensor-participant correlators. Participant data (e.g., an individual profile) may be stored in a server, in tag memory, in sensor memory, or in other storage accessible via a network or communication system, including tag data or additional stored sensor data as explained previously.

In some embodiments, by comparing data accessed using a sensor-participant correlator, the receiver hub/locate engine 108 may associate a participant with a sensor information packet received from a sensor, and/or may associate a participant with such sensor. Because the receiver hub/locate engine 108 may associate a sensor position estimate with a sensor information packet, the receiver hub/locate engine 108 may also estimate a participant position for the associated participant.

In another embodiment, by comparing data accessed using a tag-sensor correlator, the receiver hub/locate engine 108 may associate a sensor with a tag data packet received from a RF location tag 102. Because the receiver hub/locate engine 108 may associate a location estimate with a tag data packet, the receiver hub/locate engine 108 may also create a sensor location estimate for the associated sensor. By comparing a location estimate for a RF location tag with a sensor location estimate or a sensor position estimate, the receiver hub/locate engine 108 may associate a RF location tag with a sensor, or may associate a tag data packet with a sensor information packet. The receiver hub/locate engine 108 could also determine a new or refined tag-sensor correlator based on this association.

In still another embodiment, by comparing a location estimate for a RF location tag with a participant location estimate or a participant position estimate, the receiver hub/locate engine 108 may associate a RF location tag with an participant, or may associate a tag data packet with a participant. The receiver hub/locate engine 108 could also determine a new or refined tag-participant correlator based on this association.

In one embodiment, by comparing a location estimate for a sensor with a participant location estimate or a participant position estimate, the receiver hub/locate engine 108 may associate a sensor with a participant, or may associate a sensor information packet with a participant. The receiver hub/locate engine 108 could also determine a new or refined sensor-participant correlator based on this association.

Data derived or extracted from tag signals transmitted from one or more RF location tags is referred to herein as "tag derived data" and shall include, without limitation, tag data, tag UID, tag-participant correlator, tag-sensor correlator, tag data packets, blink data, time measurements (e.g. time of arrival, time difference of arrival, phase), signal measurements (e.g., signal strength, signal direction, signal polarization, signal phase) and tag location data (e.g., including tag location estimates). Tag derived data is not derived by the RF location tag, but rather, is derived from information transmitted by the RF location tag. Information or data derived or extracted from sensor signals transmitted from one or more sensors is referred to herein as "sensor derived data" and shall include, without limitation, sensor UID, additional stored sensor data, sensor-participant correlator, environmental measurements, sensor information packets, position calculations (including sensor position estimates), position information, identity information, tag-sensor correlator, and associated sensor data. Data derived or extracted from stored participant data is referred to herein as "participant profile information", or simply "profile information" and shall include, without limitation tag-participant correlator, sensor-participant correlator, identity information, name, uniform number and team, biometric data, tag position on participant. In various embodiments, the receiver hub/locate engine 108 may transmit tag derived data, sensor derived data, participant profile information, various combinations thereof, and/or any information from the GIS, the field database, the monitored area database, and the participant database to the receiver processing and analytics system 110.

Example Receiver Hub and Receiver Processing and Distribution System

Figure 4:
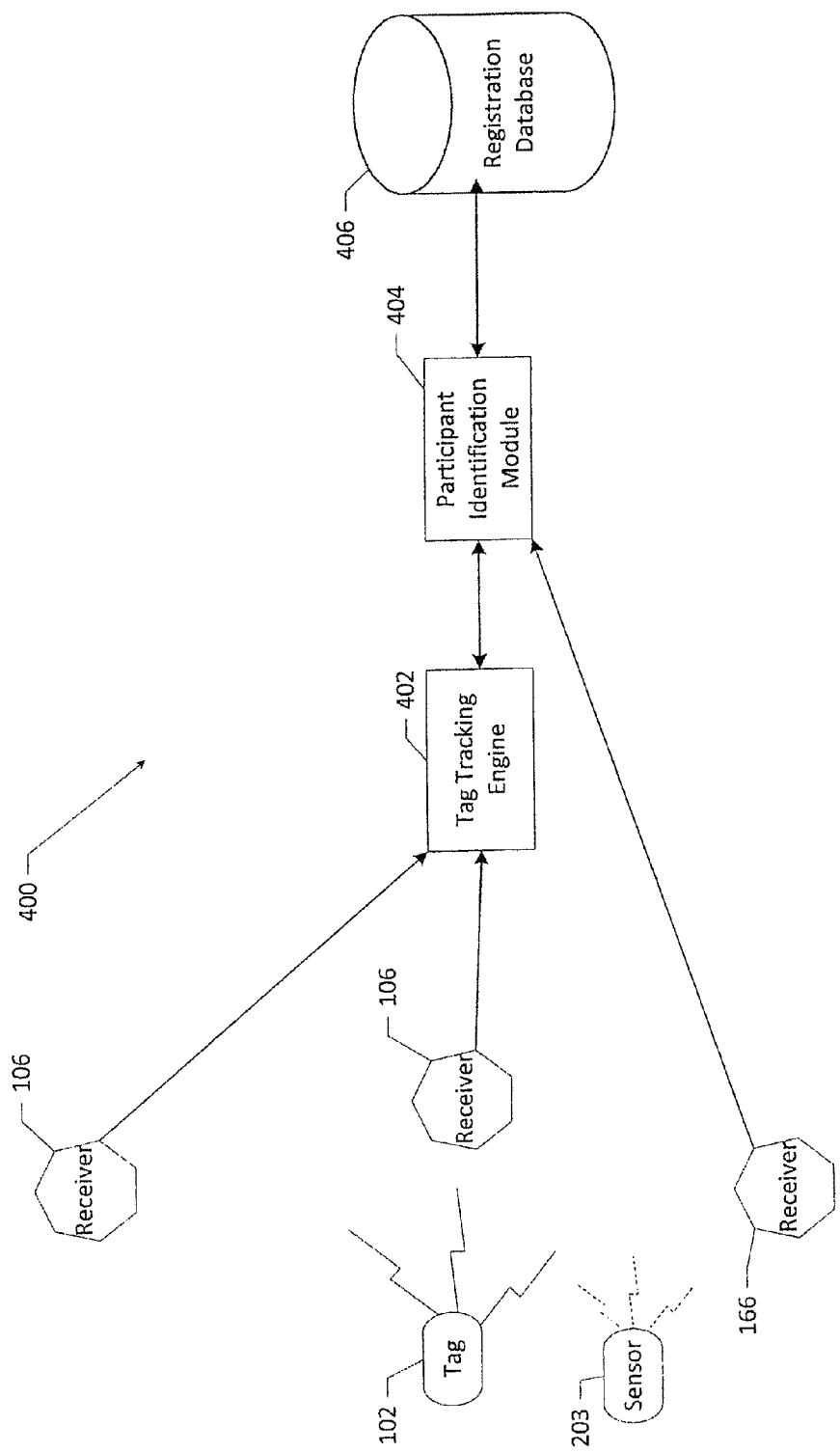
FIG. 4 illustrates an exemplary system for associating tags with participants in accordance with some embodiments of the present invention.

FIG. 4 illustrates an exemplary system 400 for associating a tag and/or sensor 203 with a participant in accordance with some embodiments of the present invention. The depicted system 400 may be distributed across a receiver hub 108 and a receiver processing and distribution system 110 of the type depicted in FIG. 1. In alternative embodiments, the system 400 may be housed or located in a single housing or unit. In still further embodiments, the system 400 may be distributed among multiple additional housings or units depending upon the application and other design parameters that will be apparent to one of ordinary skill in the art in view of this disclosure.

The performance analytics system 400 of FIG. 4 may include a plurality of tags 102, and sensors 203, associated with participants (e.g., players, officials, balls, field markers, etc.), a plurality of receivers 106 and/or sensor receivers 166 positioned within a monitored environment, a tag tracking engine 402, a participant identification module 404, and a database of tag registrations 406.

In an exemplary system 400, such as illustrated in FIG. 4, the plurality of tags 102 (and sensors 203) may be attached to a participant as discussed in connection with FIGS. 2A-C. In some embodiments, the plurality of tags 102 may be activated and deactivated as needed, such as before and after a game or when damaged or to replace batteries, power supplies, local memory, etc. Each of the tags 102 may transmit data, including a unique ID and other tag derived data, which is received by one or more of the receivers 106. In some embodiments, the receivers 106 may be configured with appropriate RF filters, such as to filter out potentially interfering signals or reflections proximate the field of play or other environment to be monitored.

Each of the receivers 106 may receive tag signals transmitted from the tags 102 and transmit tag derived data to the tag tracking engine 402. In the depicted embodiment, a sensor receiver 166 receives sensor signals transmitted from the sensors 203 and transmits sensor derived data to a participant identification module 404. The tag tracking engine 402 may collect the tag derived data from the receivers 106 and compute tag location data for the tags 102 as discussed above in connection with FIG. 1. The tag location data may then be provided to the participant identification module 404 that may use the tag location data and, optionally, received sensor derived data, to associate a particular tag and/or sensor with a particular participant.

Associations between the tags 102, sensors 203 and particular participants may be stored within a registration database 406. The registration database 406 may include a list of unique identifiers for the particular tags and/or sensors and information indicating which tags/sensors are associated with which participants. For example, the registration database 406 may include data linking a particular set of tags with a particular player (e.g., tag-individual correlators), a particular piece of player equipment (e.g., tag-equipment correlators), a particular game ball (e.g., tag-ball correlators), a particular sensor (e.g., tag-sensor correlators) or the like. The registration database 406 may further include data linking a particular set of sensors with a particular player (e.g., sensor-individual correlators), a particular piece of player equipment (e.g., sensor-equipment correlators), a particular game ball (e.g., sensor-ball correlators), a particular tag (e.g., tag-sensor correlators) or the like.

The registration database 406 may be populated with the association for each tag and/or sensor at the time the tag/sensor is registered and/or activated for the particular participant. Tags/sensors may also be re-associated or real-located as needed. For example, a malfunctioning tag may be replaced during a game with a replacement tag. Embodiments may function to associate the replacement tag with the same participant from which the malfunctioning tag was removed. Embodiments may further function to associate the replacement tag with one or more sensors that were previously associated with the replaced or original tag.

In some embodiments, data from one or more of the sensors (e.g., a proximity detector, proximity label, etc.) is used to determine the association between a particular tag and a particular participant. The participant identification module 404 may receive the sensor derived data and data from the tag tracking engine to determine correlations between the identity of the participant and an identifier associated with the tag. Upon determining this correlation, an entry for the particular tag-participant association (e.g., a tag-participant correlator) may be created within the tag registration database 406.

The foregoing description describes various example techniques for determining participant associations for one or more unassociated or unallocated RF location tags. While not discussed in detail below to avoid duplication, it will be readily apparent to one of ordinary skill in the art that the inventive concepts described below may also be applied to determining participant or tag associations for one or more unassociated or unallocated sensors.

Example proximity detectors and proximity labels that may be used for determining these tag associations may include camera sensors, biometric sensors, bar code readers, RFID readers, other RFID tags, or the like. As an example, embodiments may include the ability to determine a location of an unallocated tag. For example, the tag tracking engine 402 may detect the presence of a tag not associated with any particular participant (e.g., in the case of an unassociated replacement tag). The tag tracking engine 402 may be operable to identify the location of the unassociated tag, and to direct a camera sensor (e.g., a proximity detector) to view the location of the unassociated tag. The camera sensor may be employed to detect the presence of one or more participants at the location of the unassociated tag, and the participant identification module may be operable to determine the participant to be associated with the unassociated tag based on which participants are present (e.g., if it can be determined that all but one of the visible participants at the location have all of their associated tags accounted for, then the participant identification module 404 may associate the unassociated tag with the one participant with an unaccounted-for tag).

As another example embodiment, the proximity detectors may include biometric sensors. For example, upon replacing a tag a participant may provide biometric data via a fingerprint reader, retinal scanner, facial recognition scanner, or the like. The biometric data may be provided to the participant identification module 404 to determine the identity of the participant. For example, the participant identification module 404 may access a biometric database (not pictured) containing biometric data for a particular set of participants. The biometric data may be matched to a particular participant. The biometric scanner may further send an identifier for the particular tag to be associated with the particular participant to the participant identification module 404, such as via a wireless network connection, and the particular tag identifier may be associated with the particular participant within the registration database 406.

As yet another example embodiment, the positioning of two or more proximity detectors, receivers 106, or sensor receivers 166 may be used to correlate a tag or sensor to a participant. For example, participants may enter a field or zone in a particular order (e.g., players leaving the locker room in a single file manner via a tunnel), and the order may be known to the system. A receiver 106 (or optionally a proximity detector or sensor receiver 166) may be strategically positioned to read tags (or sensors) affixed to each participant as they pass by the receiver in the particular order, such that the participant identification module 404 associates the tags or sensor with the particular participants in the order in which the tags or sensors are read.

In yet further embodiments, a sensor 204 or, more specifically, a proximity detector may be a device used to configure tags for use by participants. For example, the sensor 203 may be a handheld or mobile device employed by a user to provide data to the participant identification module 404 indicating that a particular tag should be registered with a particular participant. The mobile device may provide the ability to transmit identification data (e.g., sensor derived data, identify information, time of sensing, etc.) to the participant identification module when a tag is replaced. The mobile device may provide the capability to indicate which tag for which user is being replaced (e.g., left shoulder pad tag for player A, or right knee tag for player B), and an identifier (e.g., tag UID) associated with the tag that is being replaced. In some embodiments, the mobile device may be functional to receive environmental measurements, such as biometric data as described above, and transmit the environmental measurements to the participant identification module 404 for use in associating the tag with the particular participant. In some examples, the mobile device may take the form of a DartWand that is operable to configure one or more tags at distances up to 60 cm and detect tag emissions up to 150 m. An exemplary DartWand manufactured by Zebra Technologies is the Zebra DartWand Module, a small device used to configure and inventory DartTags that turns tags on and off and sets their blink rate to one of a wide range of rates.

In yet further embodiments, the participant identification module 404 may associate a particular tag with a particular participant by monitoring the tag location received from the tag tracking engine 402, and deriving the identity of the participant based on the locations of the other tags in relation to the particular tag. For example, the participant identification module 404 may determine that a particular unassociated tag is consistently present in proximity to a set of assigned tags corresponding to a particular participant, and thus it may be appropriate to associate the unassociated tag with the particular participant. In this way, for example, a replacement tag positioned on equipment worn by a participant could be automatically associated with the participant based on the replacement tags consistent proximity to other tags worn by the participant. Embodiments may further utilize the techniques described above with respect to determining which players are "missing" tags to assist with determining the appropriate participant for assignment.

In yet further embodiments, the participant identification module 404 may associate a particular tag with a particular participant based on a unique signal received from the participant or equipment associated with a participant. In a first example, a proximity label, e.g., a passive RFID label, may be stitched or otherwise attached to a jersey or other identifying piece of equipment associated with a participant, the passive RFID label being configured to identify the identifying piece of equipment, such as the jersey number, when read by a proximity detector or other sensor, such as a RFID reader.

In yet further embodiments, the participant identification module 404 may associate a particular tag with a particular participant based on an identifying number included as part of tag derived data (e.g., a tag UID, tag-participant correlator, or a variable field) in some or all transmitted tag signals. In some embodiments, such an identifying number transmission may be transmitted in a first transmitted tag signal from a particular tag.

Figure 5:
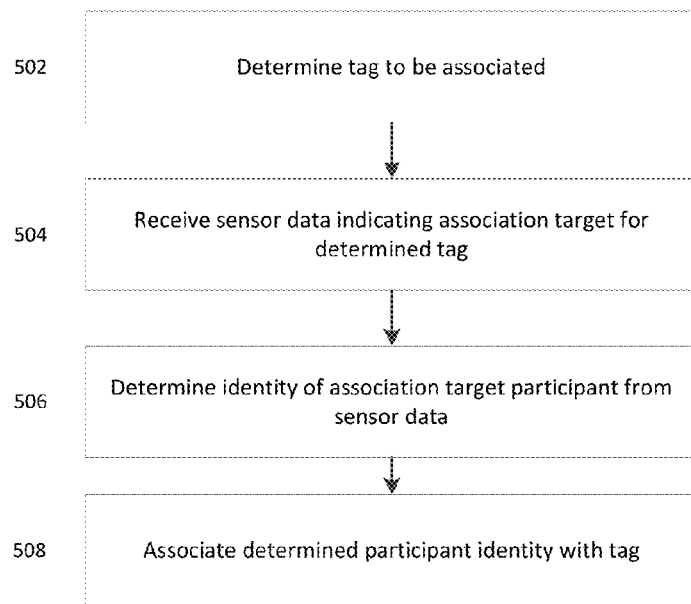

FIG. 5 illustrates a flowchart of an exemplary process for associating a tag with a participant in accordance with some embodiments of the present invention. The process may start at action 502, where a determination is made as to which tag should be associated with a participant. This determination may be made based on sensor derived data received from one or more sensors (e.g., a user mobile device used to indicate to a system that a new tag has been given to a participant (e.g., give to a player or installed in a player's equipment)), based on detection of an unassociated tag (e.g., based on receiving a response from a tag not currently associated with a particular participant), or the like. The tags 102 (and sensors 203) may be attached to participants, such as to players, officials, balls, field markers, penalty flags, other game equipment, and reference markers (e.g., boundary defining reference markers) on a field of play, but until the tag is associated with a particular participant, a tag tracking module may be unable to determine how tag data received from the unassociated tag should be interpreted. For example, a tag tracking module may be able to determine tag location data or other tag derived data for an unassociated tag, but may not be able to determine participant location data because it cannot associate a particular participant with the unassociated tag. In some embodiments, each participant may be associated with one or more tags 102 (e.g., multiple tags 102 may be attached to an individual player's equipment, such as to provide more accurate location and multi-dimensional location or orientation data). The determination performed at action 502 may include determining or receiving an identifier for the particular tag to be associated.

At action 504, sensor derived data, such as from the sensors 204, may be received. The sensor derived data may be transmitted from various sensors, including but not limited to RFID readers, biometric scanners, video capture devices, and any other sensor discussed in connection with FIGS. 3A-3E.

At action 506, the sensor data may be used to determine the identity of the participant. For example, the method may access a repository of participant information (e.g., a participant profile) to associate a participant name (e.g., derived from text data provided by a mobile application where user has input a player name), a participant biometric scan (e.g., derived from a fingerprint sensor), or other participant information (e.g., a video capture of a player's jersey number), with a particular participant. At action 508, the unassociated tag may be associated with the participant identified at action 506, such as by creating an entry within a registration database 406 that links a unique identifier for the tag with the identified participant.

FIGS. 6-10 will now be discussed in further detail. These figures describe example embodiments of methods for determining the identity of a participant for association with a tag in accordance with embodiments of the present invention. These methods may be employed to determine which participant should be associated with which tag. It should be readily appreciated that these methods or elements thereof may be employed alone or in combination with one another to assist with determining the identity of a particular participant for association with a particular tag. These methods are not intended to be exhaustive or exclusive, and various other methods and techniques, alone or in combination with the disclosed methods and elements thereof, may also be utilized to assist with associating tags with participants.

FIG. 6 illustrates a flow chart of an exemplary method 600 for determining an identity of a participant based on the location of an unassociated tag and one or more associated tags proximate to the unassociated tag. The method 600 may be operable to determine the identity of the participant by inference, including determining which participants are proximate to the location of the unassociated tag, and then eliminating participants who are unlikely to be associated with the unassociated tag. In some embodiments, the method 600 may be employed in a scenario where several, most, or all but one tag have already been associated with a participant, and a single tag or a small minority of tags remain unassociated. For example, where a participant is experiencing a malfunction of a particular tag (e.g., a single shoulder pad tag is damaged), the method 600 may be operable to associate a replacement tag with the particular participant for which the replacement tag is replacing the malfunctioning tag. The method 600 may be performed, for example, by a participant identification module 406 as described above with respect to FIG. 4.

At action 602, a location is determined for an unassociated tag. The location of the unassociated tag may be determined, for example, by an RF locating system such as described above with respect to FIG. 1. At action 604, associated tags proximate to the unassociated tag are identified. For example, the method may be able to determine the location of each tag used by the system at any given time, and may thus be able to identify which tags are within a particular radius of the unassociated tag (e.g., 3 feet, 10 feet, 10 yards).

At action 606, the identity of a participant that corresponds to the proximate associated tags may be determined. These identities may be used to constrain the number of possible participants to which the unassociated tag may correspond. However, it may not always be possible to conclusively determine a participant identity based solely on the location of nearby associated tags, since participants may be too close for an accurate determination (e.g., players congregating on a sideline). As such, further processing or determination may be used to determine the identity of the particular participant to which the unassociated tag should be associated.

At action 608, the participants associated with the proximate tags may be used to determine the identity to which the unassociated tag should be associated. For example, as described above, the participants associated with the proximate tags may be used to constrain the set of participants to which the unassociated tag will be associated. Other factors may then be employed to identify the particular participant for association. For example, the system may determine that one of the participants associated with one of the tags proximate to the unassociated tag is only providing valid data from four out of five of their associated tags, while the other participants associated with the proximate tags are providing valid data for all five of their tags. As such, the system may infer that the unassociated tag should be associated with the participant who is only providing data from four out of five tags, as the unassociated tag is likely to have been provided as a replacement for the malfunctioning tag.

FIG. 7 illustrates a flowchart of an exemplary process for using visual information to determine an identity of a participant for association with a particular tag. The method 700 may be employed to determine the identity of a particular participant by leveraging the ability to determine the location of a particular unassigned tag in conjunction with a video capture device (e.g., a camera) operable to capture visual data corresponding to the determined location. The method 700 may be performed, for example, by a participant identification module, such as the participant identification module 406 described above, in conjunction with one or more camera sensors, such as may be provided by one or more of the proximity detectors described above.

At action 702, a location is determined for an unassociated tag. As described above, the tag location data may be determined using a RF locating system as described above with respect to FIG. 1. At action 704, visual data may be captured for the location corresponding to the unassociated tag. For example, a camera or other sensor (e.g., a proximity detector) may be directed by an apparatus to a location (e.g., a particular coordinate of the monitored area 100, such as the 20 yard line of a playing field or sideline) determined at or near the location of the unassociated tag. This visual data may be used to derive which participant should be associated with the unassociated tag. For example, the visual data may identify one or more players, officials, or other participants that are at the location of the unassociated tag.

At action 706, the visual data may be used to determine the identity of the participant. For example, the visual data may be analyzed using various optical character and/or pattern recognition technologies to identify participants. For example, players may be identified based on player jersey numbers, player names on the back of their jerseys, jersey colors, and the like, and officials may be identified based on their striped uniforms and a letter indicating their title (e.g., "R" for referee, "U" for umpire, "H" or "HL" for head linesman). As described above, the participants identified using the visual data may be used to constrain the possible participants to which the unassociated tag may be associated. In the event that the proper participant cannot be determined exclusively using the visual data, various other techniques and methods may be employed to further discern which of the participants seen in the visual data should be associated with the unassociated tag.

FIG. 8 illustrates a flowchart of an exemplary method 800 for associating an unassociated tag with a particular participant by using a set of known identity calibration data. The method 800 may be operable to provide an efficient way to associate tags with participants, such as prior to a game or in another environment where a large number of tags are to be associated with particular participants. The method 800 may leverage a scenario where a particular order or other set of participant identities are known to facilitate association of tags with the particular participants. For example, players may travel from a locker room to a field through a narrow tunnel prior to a game. If the order in which the players will navigate this tunnel is known, then it may be possible to employ receivers, sensor receivers, or other sensors such as proximity detectors (e.g., RFID readers) within the tunnel to associate the tags for each player with the particular player as they traverse the tunnel and the unassociated tags enter within range of the applicable receiver, sensor receiver, proximity detector, etc.

At action 802, the known identity calibration data is received. For example, the known identity calibration data may comprise an order of participants as they will be traveling through a tunnel or otherwise passing a receiver or proximity detector.

At action 804, a tag identifier for an unassociated tag is received. Because the order of the participants is known, it may be possible for the method 800 to determine to which participant the unassociated tag corresponds. For example, the first unassociated tag (i.e., the first tag identifier or tag UID received at a tunnel based receiver) may correspond to the first player on the list to take the field. At action 806, the identity of the participant corresponding to the order specified in the known identity calibration data is associated with the unassociated tag identifier (i.e., a tag-participant correlator may be stored to the tag, the registration database, or both). It should be readily appreciated that the method may be repeated for each participant included in the known identity calibration data, with the second unassociated tag or tags being associated with the second participant in the listed order, and so on.

FIG. 9 illustrates a flowchart of an exemplary method 900 for using biometric data to associate a particular tag with a particular participant. As described above, a participant identification module may access a set of participant biometric data to determine participant identities based on biometric data received from one or more sensors. For example, participants may have fingerprints or retinal scans stored in a database, such that when a tag is to be associated with a participant, the participant provides their biometric data and the unassociated tag is associated with the participant that corresponds to the biometric data.

At action 902, the tag identifier is received for an unassociated tag. The unassociated tag may be identified by scanning the tag at the time of association with a participant (e.g., using an RFID reader coupled to the biometric scanner), by a priori knowledge of the system relating to the tag (e.g., the system may be aware of the order in which new tags will be assigned, such that the system can infer the identifier for the next tag when receiving a new set of biometric data for performing a tag association operation), or by various other methods.

At action 904, biometric identity information is received. For example, as described above, biometric identity information such as a retinal scan or a fingerprint may be received from a biometric scanner (e.g., proximity detector). In some embodiments, the biometric scanner may be coupled to a client device (e.g., a fingerprint reader coupled to a smartphone used by a technician on a sideline), or as part of the client device itself (e.g., a smartphone camera providing visual data used for facial recognition). In some embodiments, the biometric scanner may be a separate device. For example, a biometric scanner may include a fingerprint reader placed in a tunnel between a player locker room and a game field, such that as players travel down the tunnel they scan their fingerprint at the same time as any RF location tags affixed to their equipment are transmitting to one or more receivers.

At action 906, the biometric identity information is used to determine the participant identity. For example, the biometric identity information may be used to perform a lookup on a database of biometric data associated with one or more of the participants. As the participant identities are determined, the unassociated RF location tags may be associated with the participant identities corresponding to the fingerprint data.

Figure 10:
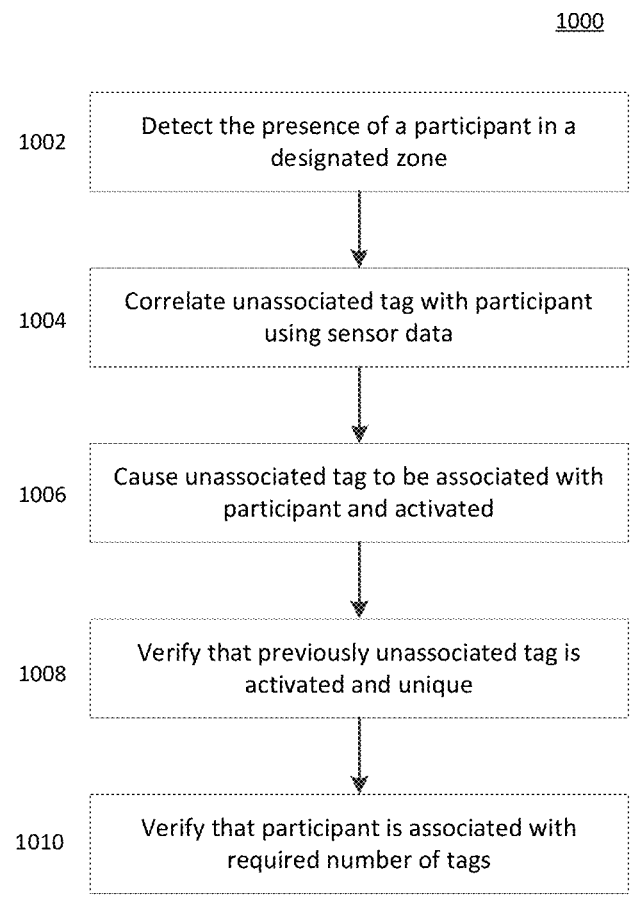

FIG. 10 illustrates a flowchart of an exemplary method 1000 for associating (e.g., registering and/or activating) a tag with a participant in accordance with example embodiments. As described above, embodiments may provide for the ability to associate a tag with a participant by determining that the participant is in a particular designated zone of the monitored area. For example, a participant may be asked to enter a designated zone to isolate the participant from other participants on a playing field sideline, a locker room, an entrance zone, a registration zone and/or the like to reduce the possibility of interference or cross-talk from tags associated with the other participants. Additionally or alternatively, participants may enter or pass through a designated zone such as a calibration area to initially register or activate tags prior to a game (e.g., the locker room tunnel example described above). The method 1000 may provide tag association functions by determining that a participant has entered a designated zone, determining an identity of the participant, and verifying that a tag is properly associated with the participant.

At action 1002, the presence of a participant may be detected within a designated zone. Detection of the participant may be performed by identifying the presence of one or more tags within the designated zone, such as by a receiver or a proximity detector including but not limited to a WherePort, a DartWand, or the like, which may or may not be coupled to various client devices such as laptop computers, tablet computers, smartphones, or the like. Additionally or alternatively, the presence of the participant may be detected by other methods, such as by visual sensors, biometric sensors, manual user input, or the like.

At action 1004, an identity for the participant may be determined based on input received from one or more sensors. In some embodiments, criteria may be established for a particular event (e.g., participants must have a certain minimum number of tags, or a certain number of tags of a particular type or configuration), and the association of the tag with the participant may include analysis of these criteria. For example, for a football game, the criteria may specify that certain tags should be configured within the participant's shoulder pads or helmet, and thus a certain type of number of tags should be used, while such a configuration would not be appropriate for a soccer game, as different equipment would be used. As such, the process of determining an identity of the participant may include not just determining who the participant is, but also the role of the participant and thus tag configuration based on criteria established for the particular event. In some embodiments, the event criteria may be determined based on the identity of the participant (e.g., identifying the participant is a player on a football team), while in other embodiments the event criteria may be determined based on extrinsic information (e.g. the system is configured in a "football" mode). Example methods for determining the identity of the participant may utilize various visual, biometric, or other sensors as described above and throughout the application.

At action 1006, the identity of the participant as determined at action 1004 may be associated with the previously unassociated tag. For example, the participant may be associated with an identifier for the previously unassociated tag in a registration database, as described above with respect to FIG. 4. As described above, the process of associating the tag with the participant may include activation of the tag, enabling the tag to be used to determine a location of the participant.

At action 1008, the method 1000 may verify that the previously unassociated tag (now associated with the participant) is functioning properly and is unique. For example, the method may identify that the tag is not using a duplicate identifier of another tag, and that the method is able to track the location of the tag. The verification process may include various authentication and calibration processes to ensure the reporting of accurate data and that the new associated tag is not malfunctioning.

At action 1010, the method 1000 may verify that the participant is properly set up for the particular event. For example, the method 1000 may identify the number of tags associated with the participant, and that the required number of tags are activated and reporting accurate data for the participant. This process may include analysis of event criteria specifying the proper configuration for participants in the event. The method 1000 may end after verifying the configuration of the participant, allowing the participant to be properly monitored by a location tracking system during the event.

Example Automatic Activation/Deactivation System

FIG. 11 illustrates an exemplary system 1100 for automatically activating and/or deactivating tags in accordance with some embodiments of the present invention. The system 1100 may leverage various embodiments as described above to more efficiently activate tags and register the tags with particular participants. In some embodiments, the system 1100 is configured to operate in an enclosed area, such as a hallway 1102. Using an enclosed area in the manner may ensure that only certain tags are within range of the system at any given time. The system 1100 may be operable in an area that one or more participants pass through. For example, the system may operate in a hallway 1102 between a locker room and a playing field, such that player participants 1108 equipped with one or more tags pass through the hallway on their way to the field.

The system 1100 may comprise an activation/deactivation device 1104, one or more receivers 1112, a receiver hub 108, and a camera 1110. The activation/deactivation device 1104 may be operable to broadcast activation and/or deactivation commands within a certain designated zone 1106. The designated zone 1106 may be configured such that a participant 1108 must pass through the designated zone 1106, such as by ensuring the designated zone 1106 spans the entire width of the hallway 1102. The activation/deactivation device 1104 may or may not be configured in communication with the one or more receivers 1112 and the receiver hub 108. For example, the activation/deactivation device 1104 may broadcast an activation command on an endless loop, without notifying other elements of the system 1100. Alternately, the activation/deactivation device 1104 may be in communication with other elements of the system. For example, the receiver hub 108 may enable, disable, or configure the activation/deactivation device 1104, such as be enabling activation or deactivation commands to be sent, by changing the commands broadcast by the activation/deactivation device 1104, or altering the range of the command broadcast. In some embodiments, the receivers may function as receivers 106 as described above with respect to FIG. 1. Additionally or alternatively, the receivers 1112 may be configured to determine an orientation of two tags relative to one another. For example, the receivers 1112 may be configured to identify a "left" tag and a "right" tag based on proximity to the group of receivers 1112.

Upon receiving an activation message from the activation/deactivation device 1104, a tag may activate itself and report to the receivers 1112. As described above, activation of the tag may include tapping an on-board power source, such as a battery. Upon activation, the tag may communicate with one or more of the receivers 1112 to enable the receivers 1112 to determine the location of the tag, and to notify the receiver hub that the tag has been activated. The receivers 1112 may communicate with the receiver hub 108 to notify the receiver hub of the activation of the tag.

In some embodiments, the camera 1110 provides visual information to the receiver hub 108. This visual information may be used to register a particular tag with a particular participant, or to determine a tag orientation for that participant (e.g., whether the tag is on the participant's left or right side). For example, the camera 1110 may provide video of players wearing jerseys passing through the designated zone 1106. The receiver hub 108 may identify which participant is passing through the designated zone 1106 based on the player's jersey number, and associate the tags present in the zone with the player.

It should be readily appreciated that various embodiments of a designated zone 1106 may be employed for activation of tags associated with a participant 1108. For example, a first embodiment may employ the camera 1110 in conjunction with the receivers 1112, the receiver hub 108, and the activation/deactivation device 1104 to detect the presence of one or more unactivated tags within the designated zone 1106. Upon detection of unactivated tags, video from the camera 1110 may be utilized to determine an identity of the participant, along with the orientation of the tags associated with the participant.

In another embodiment, the receivers 1112 may be employed to determine the orientation of tags within the designated zone 1106. Although the orientation of tags relative to one another is described by example with reference to a "left side" tag and a "right side" tag, it should be appreciated that tags can be determined based on any orientation within two or three dimensional space (e.g., top, bottom, middle, upper left, lower right, etc.). It should also be appreciated that the orientation of various numbers of tags may be identified. For example, a given player may have 10 or more tags inserted in various pieces of equipment, and the receivers 1112 may identify which tags are associated with which equipment by determining the location of each of the tags relative to one another.

In yet another embodiment, the designated zone 1106 and activation/deactivation device 1104 may be employed to activate or deactivate any tags passing through the designated zone 1106, without determining a tag orientation. For example, a designated zone 1106 may be configured across a tunnel traversed by players on the way to the playing field. As each player passes through the designated zone 1106, the activation/deactivation device 1104 may activate every tag passing through the zone. Similarly, tags may be deactivated as the players return to the locker room from the playing field. In such embodiments, the tags may be registered to particular participants prior to entering the designated zone 1106.

The activation/deactivation device 1104 may also be configured to deactivate tags. For example, at the end of a match or practice, player tags may be deactivated to conserve battery power. As players return from the playing field to the locker room, they may pass through the designated zone 1106 again, and the activation/deactivation device 1104 may broadcast a deactivation command. Tags may report to the receivers 1112 as they are deactivated to ensure the operational state of the tag is tracked by the receiver hub 108. In this manner, the tags may be efficiently activated and deactivated without the need for a particular user to individually query each tag. Depending on the embodiment, deactivating a tag to conserve battery power could involve slowing the blink rate, reducing the emitted power, reducing the size of the data packet, or even turning off the tag entirely.

FIG. 12 provides a flowchart of an exemplary process 1200 that may be used to automatically activate and/or register a tag in accordance with some embodiments of the present invention. At action 1202, the process may receive a notification that a tag has been newly activated. For example, as described above with respect to FIG. 11, a participant may have entered a designated zone and received an activation command from an activation/deactivation device.

At action 1204, visual information may be received, such as information from a camera surveying the designated zone. The visual information may include information sufficient to identify the participant, such as by facial recognition, identification of a jersey number, a biometric indicator (e.g., a fingerprint), or the like.

At action 1206, the visual information may be used to associate the newly activated tag with a particular participant. For example, the visual information may be used to identify a player. In some embodiments, the association may include further information used for identifying an orientation of the tag, such as identifying whether the tag is located on the player's right side or left side.

Example Apparatus for Implementing Embodiments

FIG. 13 shows a block diagram of components that may be included in an apparatus 1300 that may register and activate tags and provide performance analytics in accordance with embodiments discussed herein. The apparatus 1300 may comprise one or more processors, such as a processor 1302, one or more memories, such as a memory 1304, communication circuitry 1306, and a user interface 1308. The processor 1302 can be, for example, a microprocessor that is configured to execute software instructions and/or other types of code portions for carrying out defined steps, some of which are discussed herein. The processor 1302 may communicate internally using data bus, for example, which may be used to convey data, including program instructions, between the processor 1302 and the memory 1304.

The memory 1304 may include one or more non-transitory storage media such as, for example, volatile and/or non-volatile memory that may be either fixed or removable. The memory 1304 may be configured to store information, data, applications, instructions or the like for enabling the apparatus 1300 to carry out various functions in accordance with example embodiments of the present invention. For example, the memory could be configured to buffer input data for processing by the processor 1302. Additionally or alternatively, the memory could be configured to store instructions for execution by the processor 1302. The memory 1304 can be considered primary memory and be included in, for example, RAM or other forms of volatile storage which retain its contents only during operation, and/or the memory 1304 may be included in non-volatile storage, such as ROM, EPROM, EEPROM, FLASH, or other types of storage that retain the memory contents independent of the power state of the apparatus 1300. The memory 1304 could also be included in a secondary storage device, such as external disk storage, that stores large amounts of data. In some embodiments, the disk storage may communicate with the processor 1302 using an input/output component via a data bus or other routing component. The secondary memory may include a hard disk, compact disk, DVD, memory card, or any other type of mass storage type known to those skilled in the art.

In some embodiments, the processor 1302 may be configured to communicate with external communication networks and devices using the communications circuitry 1306, and may use a variety of interfaces such as data communication oriented protocols, including X.25, ISDN, DSL, among others. The communications circuitry 1306 may also incorporate a modem for interfacing and communicating with a standard telephone line, an Ethernet interface, cable system, and/or any other type of communications system. Additionally, the processor 1302 may communicate via a wireless interface that is operatively connected to the communications circuitry 1306 for communicating wirelessly with other devices, using for example, one of the IEEE 802.11 protocols, 802.15 protocol (including Bluetooth, ZigBee, and others), a cellular protocol (Advanced Mobile Phone Service or "AMPS"), Personal Communication Services (PCS), or a standard 3G wireless telecommunications protocol, such as CDMA2000 1× EV-DO, GPRS, W-CDMA, LTE, and/or any other protocol.

The apparatus 1300 may include a user interface 1308 that may, in turn, be in communication with the processor 1302 to provide output to the user and to receive input. For example, the user interface may include a display and, in some embodiments, may also include a keyboard, a mouse, a joystick, a touch screen, touch areas, soft keys, a microphone, a speaker, or other input/output mechanisms. The processor may comprise user interface circuitry configured to control at least some functions of one or more user interface elements such as a display and, in some embodiments, a speaker, ringer, microphone and/or the like. The processor and/or user interface circuitry comprising the processor may be configured to control one or more functions of one or more user interface elements through computer program instructions (e.g., software and/or firmware) stored on a memory accessible to the processor (e.g., the memory 1304, and/or the like).

In some embodiments, certain ones of the operations above may be modified or further amplified as described below. Moreover, in some embodiments additional optional operations may also be included. It should be appreciated that each of the modifications, optional additions or amplifications below may be included with the operations above either alone or in combination with any others among the features described herein.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

That which is claimed:

1. An apparatus for associating a participant identifier with an unassociated radio frequency (RF) location tag, the apparatus comprising at least one processor, and at least one non-transitory memory including computer program code, wherein the at least one non-transitory memory and the computer program code are configured, with the at least one processor, to cause the apparatus to:

receive tag derived data originating from an unassociated RF location tag;
determine unassociated tag location data for the unassociated RF location tag based on the received tag derived data;
receive second tag derived data originating from a plurality of associated RF location tags;
determine associated tag location data for the plurality of associated RF location tags based on the received second tag derived data;
determine tag proximity location data for each of the plurality of associated RF location tags by comparing the unassociated tag location data to the associated tag location data;
determine a constrained set of associated RF location tags from the plurality of associated RF location tags based on determining, by the processor, whether the tag proximity location data for each of the plurality of associated RF location tags satisfies a proximity radius;
determine a participant identifier for each associated RF location tag of the constrained set of associated RF location tags;
in a circumstance where two or more unique participant identifiers are determined from the constrained set of associated RF location tags, determine whether one of the two or more unique participant identifiers is associated with a malfunctioning RF location tag;
in a circumstance where one of the two or more unique participant identifiers is determined to be associated with the malfunctioning RF location tag, output a tag participant correlator for associating the one of the two or more unique participant identifiers with the unassociated RF location tag.

2. The apparatus of claim 1, wherein the unassociated RF location tag comprises an ultra-wideband (UWB) transmitter.

3. The apparatus of claim 2, wherein the UWB transmitter is configured to transmit a plurality of time of arrival (TOA) timing pulses.

4. The apparatus of claim 3, wherein the UWB transmitter is configured to transmit an information packet comprising 112 bits.

5. The apparatus of claim 1, wherein the proximity radius is one of three feet, ten feet, or ten yards.

6. The apparatus of claim 1, wherein the at least one processor is further configured to cause the apparatus to:
in a circumstance where only one unique participant identifier is determined from the constrained set of associated RF location tags, output a second tag participant correlator for associating the only one unique participant identifier with the unassociated RF location tag.

7. The apparatus of claim 1, wherein the tag participant correlator is configured for storing with a participant profile comprising biometric data and role data.

8. The apparatus of claim 1, wherein the tag derived data and the second tag derived data comprise time of arrival measurement data and tag information packets.

9. The apparatus of claim 1, wherein the at least one processor is further configured to cause the apparatus to:
determine whether one of the two or more unique participant identifiers is associated with the malfunctioning RF location tag by comparing a known number of participant-associated RF location tags to the second tag derived data.

10. A system for associating a participant identifier with an unassociated radio frequency (RF) location tag, the system comprising:
an unassociated RF location tag configured to transmit blink data;
a plurality of associated RF location tags, each of the plurality of associated RF location tags associated with a participant identifier, and wherein each of the plurality of associated RF location tags are configured to transmit second blink data;
a plurality of receivers that are configured to:
receive the second blink data transmitted by the plurality of associated RF location tags and receive the blink data transmitted by the unassociated RF location tag;
determine tag derived data from the blink data; and
determine second tag derived data from the second blink data;
a receiver processing and distribution system configured to:
receive the tag derived data originating from the unassociated RF location tag;
determine unassociated tag location data for the unassociated RF location tag based on the received tag derived data;
receive the second tag derived data originating from the plurality of associated RF location tags;
determine associated tag location data for the plurality of associated RF location tags based on the received second tag derived data;
determine tag proximity location data for each of the plurality of associated RF location tags by comparing the unassociated tag location data to the associated tag location data;
determine a constrained set of associated RF location tags from the plurality of associated RF location tags based on determining whether the tag proximity location data for each of the plurality of associated RF location tags satisfies a proximity radius;
identify the participant identifier for each associated RF location tag of the constrained set of associated RF location tags;
in a circumstance where two or more unique participant identifiers are identified from the constrained set of associated RF location tags, determine whether one of the two or more unique participant identifiers is associated with a malfunctioning RF location tag;
in a circumstance where one of the two or more unique participant identifiers is associated with the malfunctioning RF location tag, output a tag participant correlator for associating the one of the two or more unique participant identifiers with the unassociated RF location tag.

11. The system of claim 10, wherein the unassociated RF location tag comprises an ultra-wideband (UWB) transmitter.

12. The system of claim 11, wherein the UWB transmitter is configured to transmit blink data comprising a plurality of time of arrival (TOA) timing pulses.

13. The system of claim 11, wherein the UWB transmitter is configured to transmit an information packet comprising 112 bits.

14. The system of claim 10, wherein the proximity radius is one of three feet, ten feet, or ten yards.

15. The system of claim 10, wherein the receiver processing and distribution system is further configured to:

in a circumstance where only one unique participant identifier is determined from the constrained set of associated RF location tags, output a second tag participant correlator for associating the only one unique participant identifier with the unassociated RF location tag.

16. The system of claim 10, wherein the tag participant correlator is configured for storing with a participant profile comprising biometric data and role data.

17. The system of claim 10, wherein the tag derived data and the second tag derived data comprise time of arrival measurement data and tag information packets.

18. The system of claim 10, wherein the receiver processing and distribution system is further configured to:
determine whether one of the two or more unique participant identifiers is associated with the malfunctioning RF location tag by comparing a known number of participant associated RF location tags to the second tag derived data.

* * * * *